United States Patent
Basilion et al.

(10) Patent No.: US 12,083,191 B2
(45) Date of Patent: *Sep. 10, 2024

(54) COMPOSITION AND METHODS FOR IMAGING CELLS

(71) Applicant: CASE WESTERN RESERVE UNIVERSITY, Cleveland, OH (US)

(72) Inventors: James Basilion, Shaker Heights, OH (US); Kirti Dhingra, Cleveland, OH (US); Thomas J. Meade, Evanston, IL (US); Sarah Grace Kamper, Evanston, IL (US)

(73) Assignees: CASE WESTERN RESERVE UNIVERSITY, Cleveland, OH (US); NORTHWESTERN UNIVERSITY, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/573,570

(22) Filed: Sep. 17, 2019

(65) Prior Publication Data

US 2020/0009271 A1    Jan. 9, 2020

Related U.S. Application Data

(63) Continuation-in-part of application No. 13/502,852, filed as application No. PCT/US2010/053219 on Oct. 19, 2010, now Pat. No. 10,413,621.

(60) Provisional application No. 61/252,882, filed on Oct. 19, 2009.

(51) Int. Cl.
*A61K 49/18*     (2006.01)
*A61K 49/00*     (2006.01)
*A61K 49/08*     (2006.01)
*A61K 49/14*     (2006.01)

(52) U.S. Cl.
CPC ...... *A61K 49/1881* (2013.01); *A61K 49/0017* (2013.01); *A61K 49/085* (2013.01); *A61K 49/14* (2013.01)

(58) Field of Classification Search
CPC ............ A61K 49/00; A61K 2121/00; A61K 2123/00; A61K 49/14; A61K 49/0017; A61K 49/085; A61K 49/10; A61K 49/0002; A61K 49/1881
USPC .......... 424/1.11, 1.49, 1.65, 1.69, 1.81, 1.85, 424/1.89, 9.1, 9.2, 9.3, 9.4, 9.5, 9.6; 534/7, 10–16; 514/1, 1.1, 19.2, 19.3, 514/19.4, 19.5, 19.6, 20.9, 21.1, 21.2, 514/21.3, 21.4, 21.5, 21.6, 21.7, 21.8, 514/21.9, 21.91; 530/300
See application file for complete search history.

(56) References Cited

U.S. PATENT DOCUMENTS

| | | | |
|---|---|---|---|
| 6,217,869 B1 * | 4/2001 | Meyer | A61K 47/6897 424/178.1 |
| 9,889,199 B2 | 2/2018 | Basilion et al. | |
| 10,207,005 B2 | 2/2019 | Basilion | |
| 10,363,313 B2 | 7/2019 | Basilion | |
| 10,709,794 B2 | 7/2020 | Basilion et al. | |
| 2002/0122806 A1 | 9/2002 | Chinnaiyan et al. | |
| 2006/0088475 A1 * | 4/2006 | Duimstra | A61K 47/555 424/9.361 |
| 2008/0193381 A1 | 8/2008 | Babich et al. | |
| 2009/0061010 A1 | 3/2009 | Zale et al. | |
| 2010/0324008 A1 | 12/2010 | Low et al. | |
| 2012/0323164 A1 | 12/2012 | Kenney et al. | |

FOREIGN PATENT DOCUMENTS

| | | |
|---|---|---|
| WO | 2004/037975 A2 | 5/2004 |
| WO | 2005/099693 A2 | 10/2005 |
| WO | 2008/019052 A2 | 2/2008 |
| WO | 2008/057437 A1 | 5/2008 |
| WO | 2011/106639 A1 | 9/2011 |
| WO | 2012/016713 A2 | 2/2012 |

OTHER PUBLICATIONS

Urbanczyk-Pearson et al, Nature Protocols, vol. 3, No. 3, pp. 341-350 (Year: 2008).*
Duimstra et al, J. Am. Chem. Soc., vol. 127, pp. 12847-12855 (Year: 2005).*
Bonnet et al, AJNR Am. J. Neuroradiol., 2010, vol. 31, pp. 401-409.
Major et al, Acc. Chem. Res., 2009, vol. 42, No. 7, pp. 893-903.
Pedley et al, Methods in Molecular Science, 2004, vol. 90, pp. 491-514.
Extended Search Report for Application No. 14751113.3-1453/ 2958596, dated Oct. 10, 2016.
Kularatne, Sumith A., et al., "Synthesis and Biological Analysis of Prostate-Specific Membrane Antigen-Targeted Anticancer Prodrugs", Journal of Medicinal Chemistry, vol. 53, No. 21, Nov. 11, 2010, pp. 7767-7777, KP055103918.
Ikeda, Masato, et al., "Supramolecular hydrogel capsule showing prostate specific antigen-responsive function for :; ensing and targeting prostate cancer cells", Chem. Sci., 2010, 1, 491-498.
EP Office action for Application No. 14751113.3-1109, dated Jan. 1, 2019.
U.S. Appl. No. 16/901,874, filed Jun. 15, 2020, U.S. Non-Final Rejection dated Aug. 18, 2022, 13 pgs.

* cited by examiner

*Primary Examiner* — D. L. Jones
(74) *Attorney, Agent, or Firm* — Tarolli, Sundheim, Covell & Tummino LLP

(57) ABSTRACT

A composition for imaging a cell includes a first imaging probe and a second imaging probe that include respectively a first reporter moiety and a second reporter moiety. The first reporter moiety and the second reporter moiety form a signaling complex that produces a detectable signal when the first imaging probe and second imaging probe complex with first and second biomarkers of the cell.

12 Claims, 18 Drawing Sheets

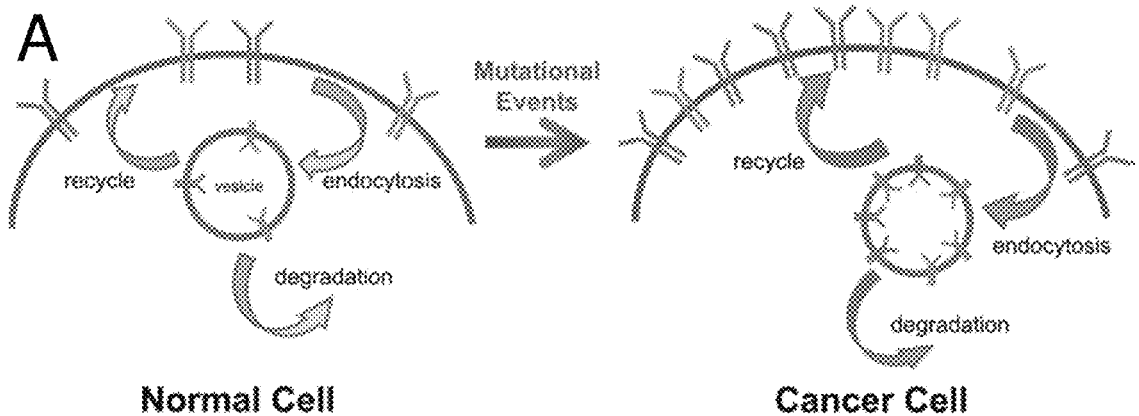
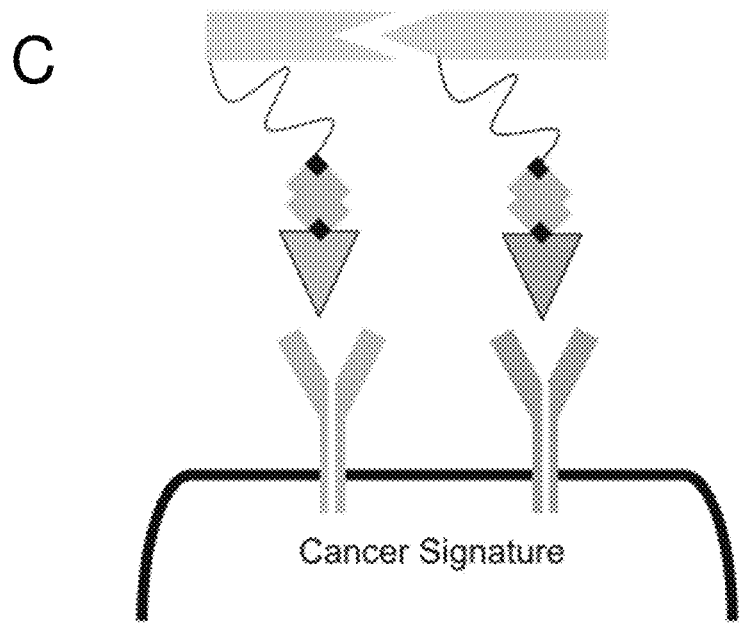
Figs. 4A-C

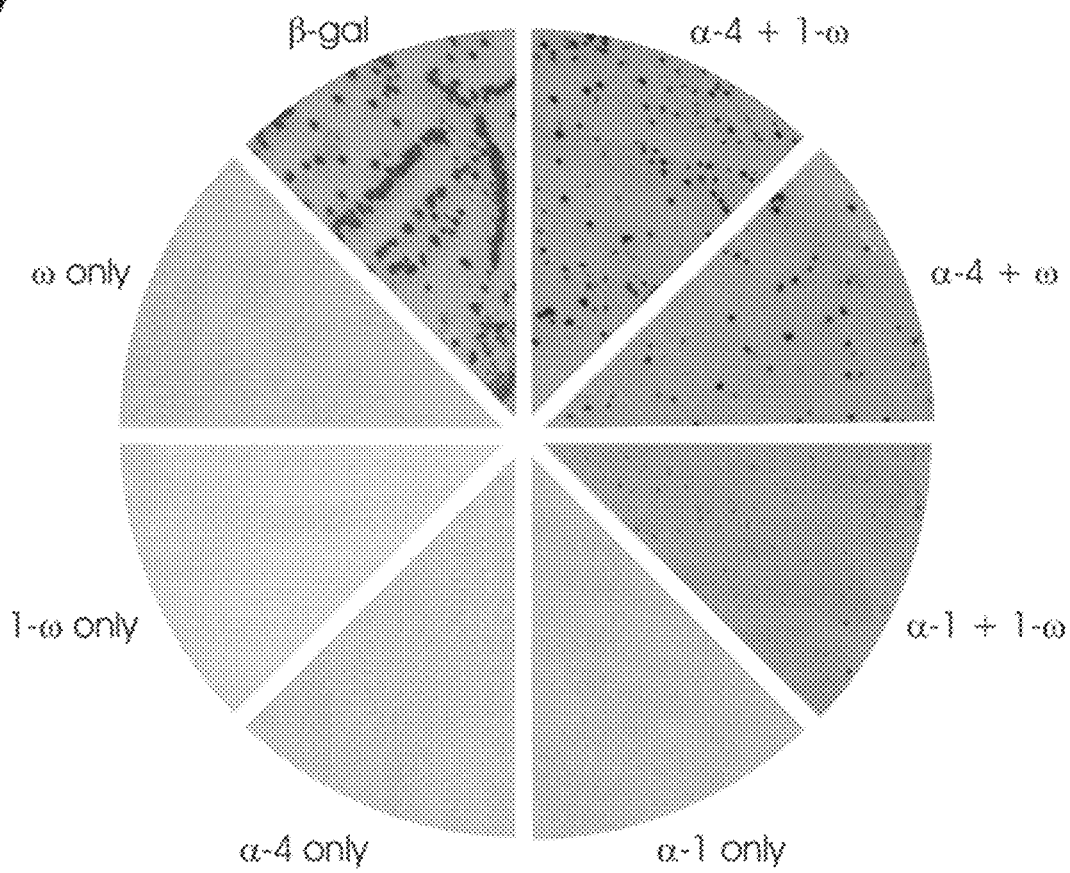
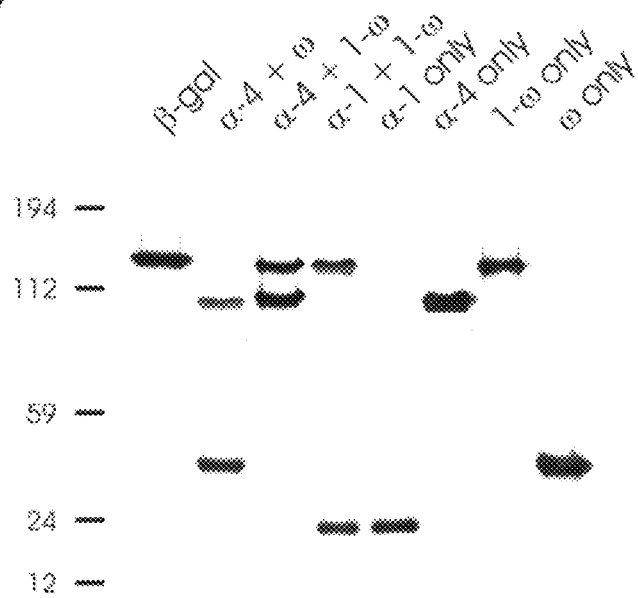
Figs. 6A-B

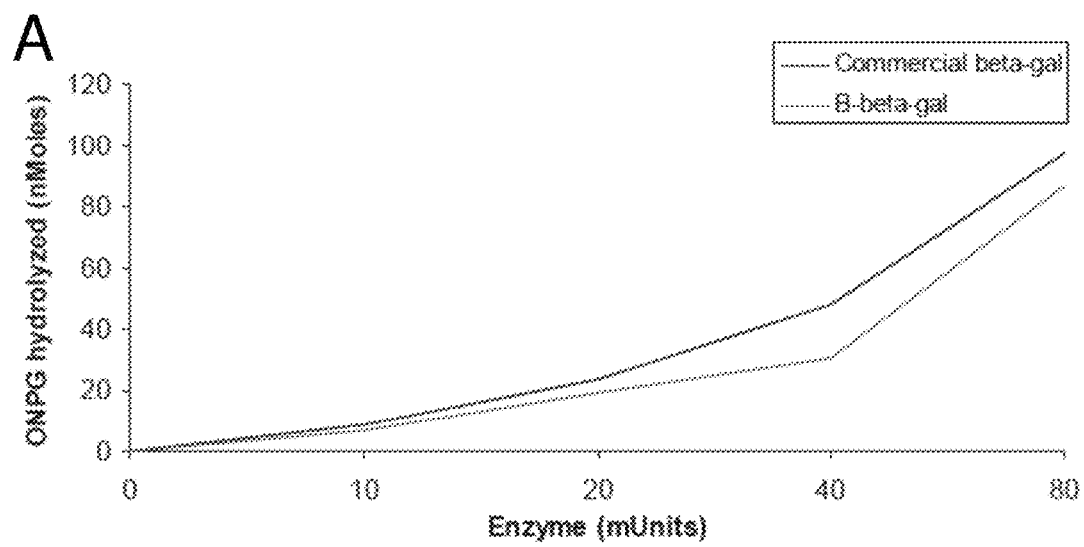
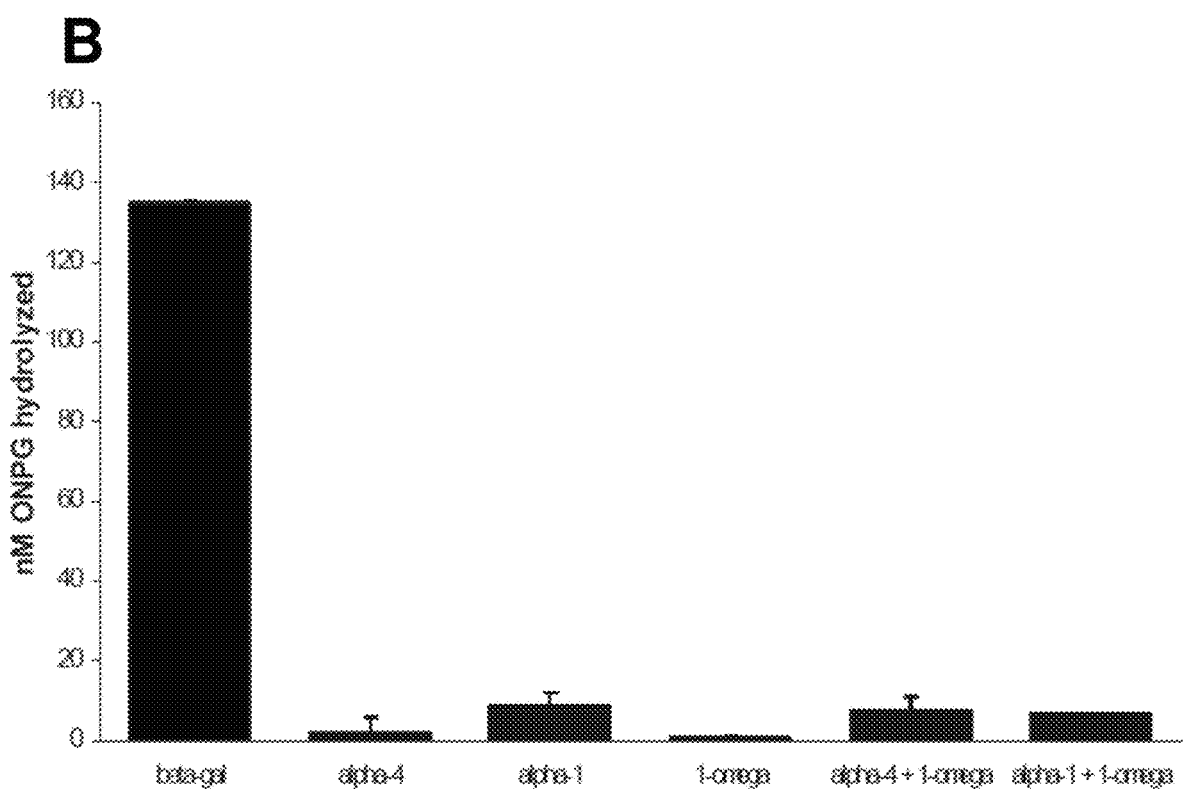
Figs. 7A-B

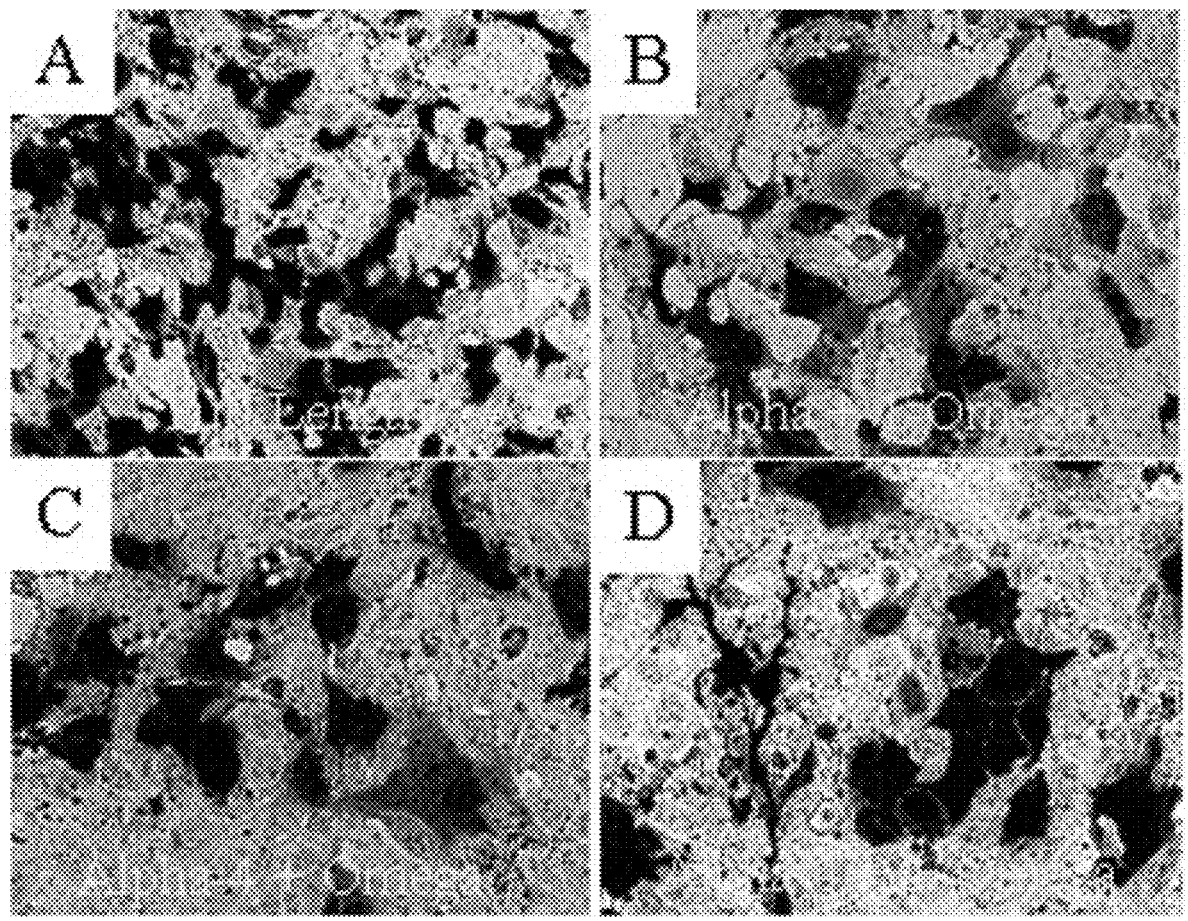
Figs. 8A-D

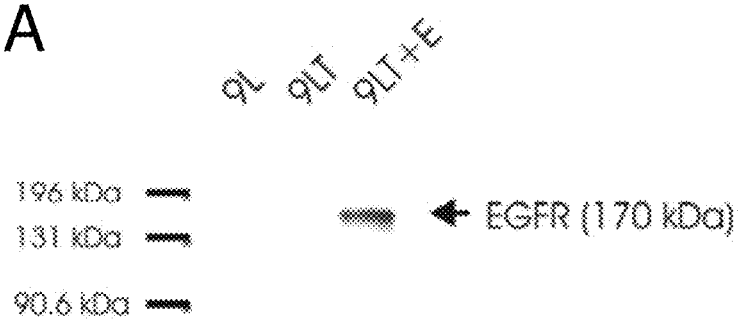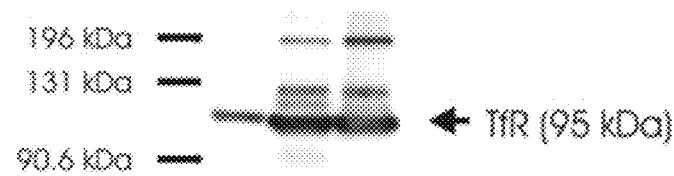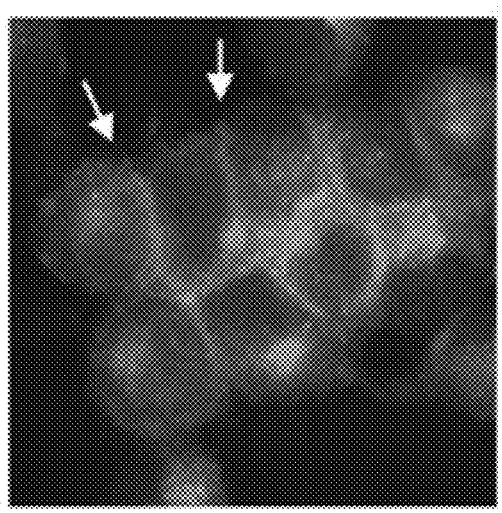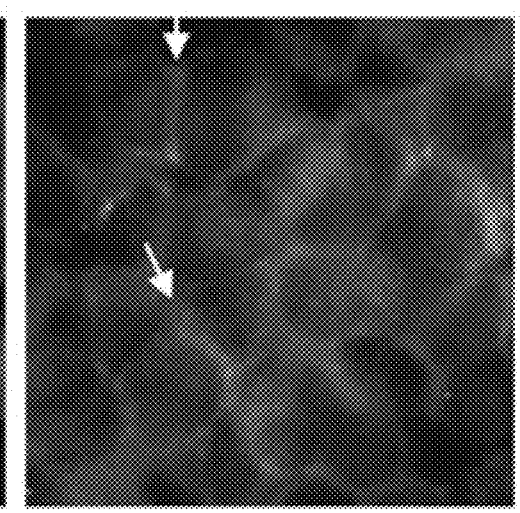
Figs. 9A-B

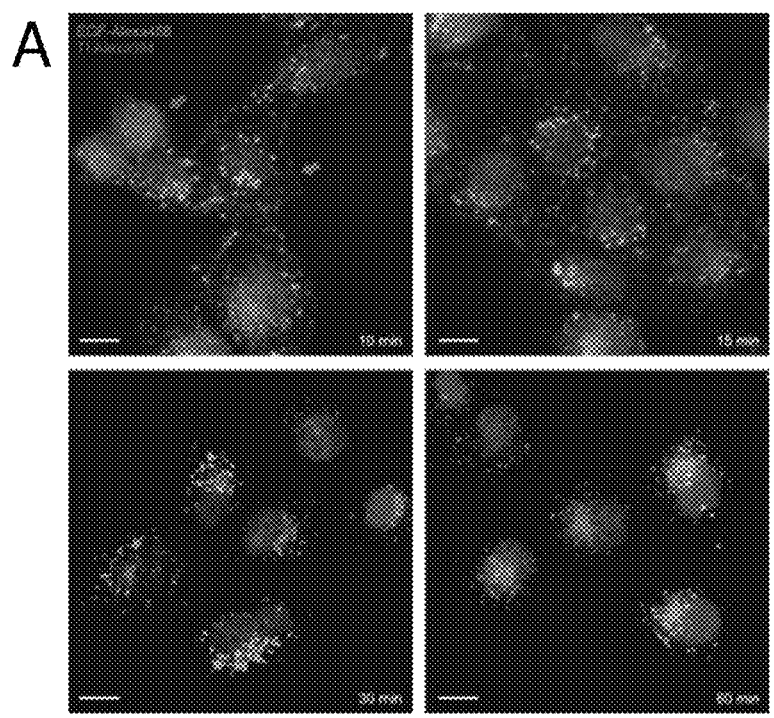
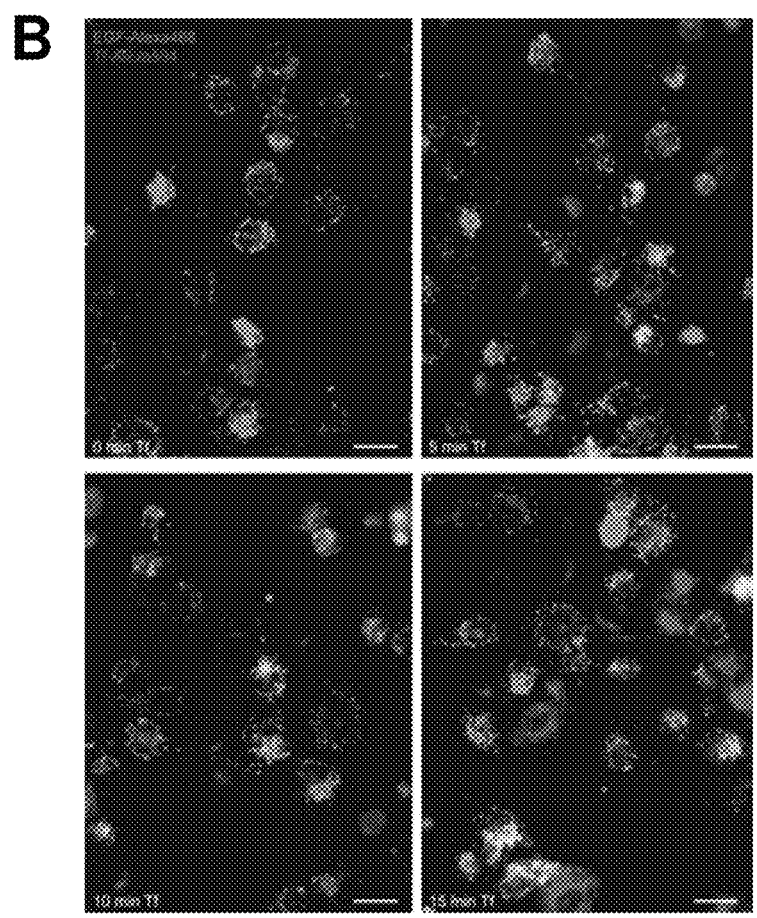
Figs. 10A-B

COMPOSITION AND METHODS FOR IMAGING CELLS

RELATED APPLICATION

This application a Continuation-in-Part of U.S. Ser. No. 13/502,852, filed Apr. 19, 2012, Now U.S. Pat. No. 10,413,621, which is a National Phase Filing of PCT/US2010/053219, filed Oct. 19, 2010, which claims priority from U.S. Provisional Application No. 61/252,882, filed Oct. 19, 2009, the subject matter, which is incorporated herein by reference.

GOVERMENT FUNDING

This invention was made with government support under EB005866, HL108795, and GM008382 awarded by the National Institutes of Health. The government has certain rights in the invention.

TECHNICAL FIELD

This application relates to compositions and methods for imaging cells, and more particularly to imaging probes for ex vivo or in vivo determination of a cell's molecular signature.

BACKGROUND

Advances in identification of biomarkers have been the hallmark of the genomic and proteomic revolutions, and should allow researchers to develop imaging tools that are both more specific and sensitive for detection of diseases or disorders. The desire to label multiple biomarkers has lead to high throughput serial identification schemes that correlate protein expression to specific types or stages of disorders, such as cancer. The results of such studies are often limited by technical variability between assays, lack of appropriate controls, and a paucity of direct interactions among the biomarkers examined. Most of these techniques are not amenable to translation into non-invasive imaging applications.

SUMMARY

This application relates to compositions and methods for imaging cells, and more particularly to imaging probes for ex vivo or in vivo determination of a cell's molecular signature. One aspect of the application relates to a composition for imaging a cell having a first biomarker and a second biomarker that is proximate to and different from the first biomarker. The composition can comprise first and second imaging probes. The first imaging probe can include a first targeting moiety that is linked to a first reporter moiety via a linker region. The first targeting moiety can specifically complex with the first biomarker. The second imaging probe can include a second targeting moiety that is linked to a second reporter moiety via a linker region. The second targeting moiety is different than the first targeting moiety and specifically complexes with the second biomarker. The first reporter moiety and the second reporter moiety can form a signaling complex that produces a detectable signal when the first and second imaging probes complex respectively with the first biomarker and the second biomarker.

Another aspect of the application relates to a composition for determining a molecular signature of a cell having a first biomarker and a second biomarker that is different than the first biomarker. The composition can comprise first and second imaging probes. The first imaging probe can include a first targeting moiety that is linked to a first reporter moiety via a linker region. The first targeting moiety can specifically complex with the first biomarker. The second imaging probe can include a second targeting moiety that is linked to a second reporter moiety via a linker region. The second targeting moiety is different than the first targeting moiety and specifically complexes with the second biomarker. The first reporter moiety and the second reporter moiety can form a signaling complex that produces a detectable signal when the first and second imaging probes complex respectively with the first biomarker and the second biomarker. The molecular signature can comprise the detectable signal.

Another aspect of the application relates to a method for imaging a cell having a first biomarker and a second biomarker that is different than the first biomarker. One step of the method can include contacting the cell with an imaging composition comprising first and second imaging probes. The first imaging probe can include a first targeting moiety that is linked to a first reporter moiety via a linker region. The first targeting moiety can specifically complex with the first biomarker. The second imaging probe can include a second targeting moiety that is linked to a second reporter moiety via a linker region. The second targeting moiety is different than the first targeting moiety and specifically complexes with the second biomarker. The first reporter moiety and the second reporter moiety can form a signaling complex that produces a detectable signal when the first and second imaging probes complex respectively with the first biomarker and the second biomarker.

Another aspect of the application relates to a method for determining a molecular signature of a cell that is associated with a disease. The cell can have a first biomarker and a second biomarker that is different than the first biomarker. One step of the method can comprise contacting the cell with an imaging composition comprising first and second imaging probes. The first imaging probe can include a first targeting moiety that is linked to a first reporter moiety via a linker region. The first targeting moiety can specifically complex with the first biomarker. The second imaging probe can include a second targeting moiety that is linked to a second reporter moiety via a linker region. The second targeting moiety is different than the first targeting moiety and specifically complexes with the second biomarker. The first reporter moiety and the second reporter moiety can form a signaling complex that produces a detectable signal when the first and second imaging probes complex respectively to the first biomarker and the second biomarker. Next, the molecular signature of the cell can be produced based on the detectable signal generated when the first and second biomarkers complex respectively with the first biomarker and the second biomarker and form a signaling complex. The molecular signature can indicate at least one of the type, stage, or severity of the disease.

Another aspect of the application relates to a method for treating a disease in a subject. One step of the method can comprise contacting a cell that is associated with the disease with an imaging composition comprising first and second imaging probes. The cell can have a first biomarker and a second biomarker that is different from the first biomarker. The first imaging probe can include a first targeting moiety that is linked to a first reporter moiety via a linker region. The first targeting moiety can specifically complex with the first biomarker. The second imaging probe can include a second targeting moiety that is linked to a second reporter moiety via a linker region. The second targeting moiety is different than the first targeting moiety and specifically complexes with the second biomarker. The first reporter moiety and the second reporter moiety can form a signaling complex that produces a detectable signal when the first and second imaging probes complex respectively to the first biomarker and the second biomarker. Next, the molecular signature of the cell can be produced based on the detectable signal generated when the first and second biomarkers complex respectively with the first biomarker and the second biomarker and form a signaling complex. The molecular signature can indicate at least one of the type, stage, or severity of the disease. The subject can then be treated based on the molecular signature.

A further aspect of the application relates to a method for treating a disease in a subject by contacting a cell associated with the disease with a therapeutic composition comprising a first therapeutic probe and a second therapeutic probe. The cell can have a first biomarker and a second biomarker that is different from the first biomarker. The first therapeutic probe can include a first targeting moiety that is linked to a therapeutic agent via a linker region. The first targeting moiety can specifically complex with the first biomarker. The second therapeutic probe can include a second targeting moiety that is linked to a release agent via a linker region. The second targeting moiety is different than the first targeting moiety and specifically complexes with the second biomarker. The release agent of the second therapeutic probe can release the therapeutic agent from the first therapeutic probe to treat the disease when the first therapeutic probe and the second therapeutic probe complex respectively to the first biomarker and the second biomarker of the cell.

BRIEF DESCRIPTION OF THE DRAWINGS

The foregoing and other features of the application will become apparent to those skilled in the art to which the application relates upon reading the following description with reference to the accompanying drawings, in which:

FIGS. 4A-C are schematic illustrations showing differential cell surface receptor expression between normal and cancer cells (FIG. 4A), an imaging probe according to one aspect of the present invention (FIG. 4B), and imaging probe complementation in a cancer cell (FIG. 4C);

FIGS. 6A-B illustrate expression of active β-gal assayed by X-gal staining (FIG. 6A) and Western blot analysis of bacteria expressing β-gal fragments (FIG. 6B). E. coli K12 ER1793 were transfected with individual β-gal fragment plasmids or combinations of plasmids that would produce a complementing full length enzyme. Bacteria were electroporated with plasmid (1 ng) for 5.2 msec at 2.5 kV. After 1 hr incubation in LB broth, bacteria were streaked on LB agar plates containing ampicillin (0.1 g/L) and X-gal (50 μg/ml). Plates were incubated at 37° C. overnight. Colonies containing active β-gal stained blue. Bacteria were lysed and whole cell lysates electrophoresed, transblotted and immunoblotted with streptavidin-HRP (1:1000 dilution). E. coli K12 ER1793 transformed with complementing pairs of β-gal plasmids express both β-gal fragments (lane 1: β-gal, 135 kDa; lane 2: α-4+ω, 100 kDa and 35 kDa; lane 3: α-4+1-ω, 100 kDa and 116 kDa; lane 4: α-1+1-ω, 20 kDa and 116 kDa; lane 5: α-1, 20 kDa; lane 6: α-4, 100 kDa; lane 7: 1-ω, 116 kDa; lane 8: ω, 35 kDa);

FIGS. 7A-C illustrate, comparison of β-gal activity of full length enzyme prepared in the laboratory versus commercially available standard (FIG. 7A), enzyme activity of β-gal protein fragments (FIG. 7B), and enzyme activity of β-gal protein fragments over time (FIG. 7C). β-gal fragments were added, either individually or in complementing pairs, to uncoated 96-well microtiter assay plates in equal molar amounts and incubated at room temperature on an orbital rocker for 30 minutes in the presence of β-gal fluorescent substrate ONPG. Minimal to no enzyme activity was observed for individual or complementing fragments in solution FIG. 7B. Enzyme activity of β-gal protein fragments over time (7C). β-gal protein fragments were added individually or in complementing pairs in the presence of ONPG over a 19 hour incubation period. Full length β-gal was optimally active at 30 minutes. All fragment combinations were inactive in solution over a 3 hour time period except the combination α-4 and ω, which gradually increased after 30 minutes;

FIGS. 8A-D are a series of phase contrast images showing C6 cells expressing full length β-gal (FIG. 8A), cells transfected with β-gal fragments α-1 and 1-ω expressing enzyme activity (FIG. 8B), cells transfected with β-gal fragments α-4 and ω expressing enzyme activity (FIG. 8C), and C6 cells transfected with β-gal fragments α-4 and 1-ω expressing enzyme activity (FIG. 8D). Rat glioma C6 cells were transiently transfected using LIPOFECTAMINE 2000 (LifeTechnologies, Inc., Carlsbad, CA) as per manufacturer's instructions with pcDNA3.1 plasmids containing either full length β-gal cDNA (1 μg) or individual β-gal fragment cDNA (1 μg each). Forty-eight hours after transfection, the cells were rinsed, fixed in paraformaldehyde, and incubated overnight with X-gal staining buffer;

FIGS. 9A-B illustrate receptor overexpression in mammalian cells. The rat gliosarcoma cell line, 9 L, was stably transfected with none, one, or two human receptors (FIG. 9A). Western-blot analysis using equal amounts of total protein from the corresponding lysates was used to determine human EGFR expression. The same blot was stripped and reprobed to determine total human transferrin receptor (TfR) protein levels. Immunolocalization of human EGFR and TfR in cells overexpressing both EGFR and TfR (FIG. 9B). Cells stably overexpressing the human receptors EGFR and TfR were stained with either monoclonal anti-EGFR (1:500 dilution; DAKO; M7298) or monoclonal anti-TfR (1:500 dilution; US Biologicals; T8199) for 1 hour at room temperature. After thorough washing with PBS, cells were counterstained for 1 hour with anti-mouse-Alexa488 (1:1000 dilution) (cell surface staining is indicated by white arrows);

FIGS. 10A-C are a series of images illustrating double labeling of EGFR and TfR with fluorophore-conjugated ligand (FIG. 10A), serial addition of fluorophore-conjugated ligands EGF and Tf increases internal receptor co-localization (FIG. 10B), and representative cell with receptor co-localization of EGFR and TfR (FIG. 10C). In FIG. 10A, cells overexpressing both human EGFR and human TfR were simultaneously incubated over time (10-60 minutes) with Alexa488-EGF (5 µg/ml) and Alexa594-Tf (50 µg/ml) at 37° C. Cells were rinsed briefly, fixed, counterstained with DAPI to visualize the nuclei, and mounted for observation (green arrow indicates EGFR localized at the cell surface and red arrow indicates rapidly internalized TfR) (photographs were captured at 40× magnification, and scale bar indicates 10 µm). In FIG. 10B, cells overexpressing both EGFR and TfR were first pre-loaded with Alexa488-EGF (5 µg/ml) for 15 minutes and then incubated with Alexa594-Tf (50 µg/ml) over increasing time at 37° C. Cells were washed, fixed, and mounted for fluorescent observation (photographs were captured at 40× magnification, and scale bar indicates 20 µm). In FIG. 10C, the cell was pre-loaded with Alexa488-EGF for 15 minutes, followed by incubation with Alexa594-Tf for 10 minutes. After fixation, the cell was counterstained with DAPI to visualize the nucleus and mounted for observation (photograph was taken at 100× magnification) (inset emphasizes receptor co-localization);

DETAILED DESCRIPTION

Figure 1:
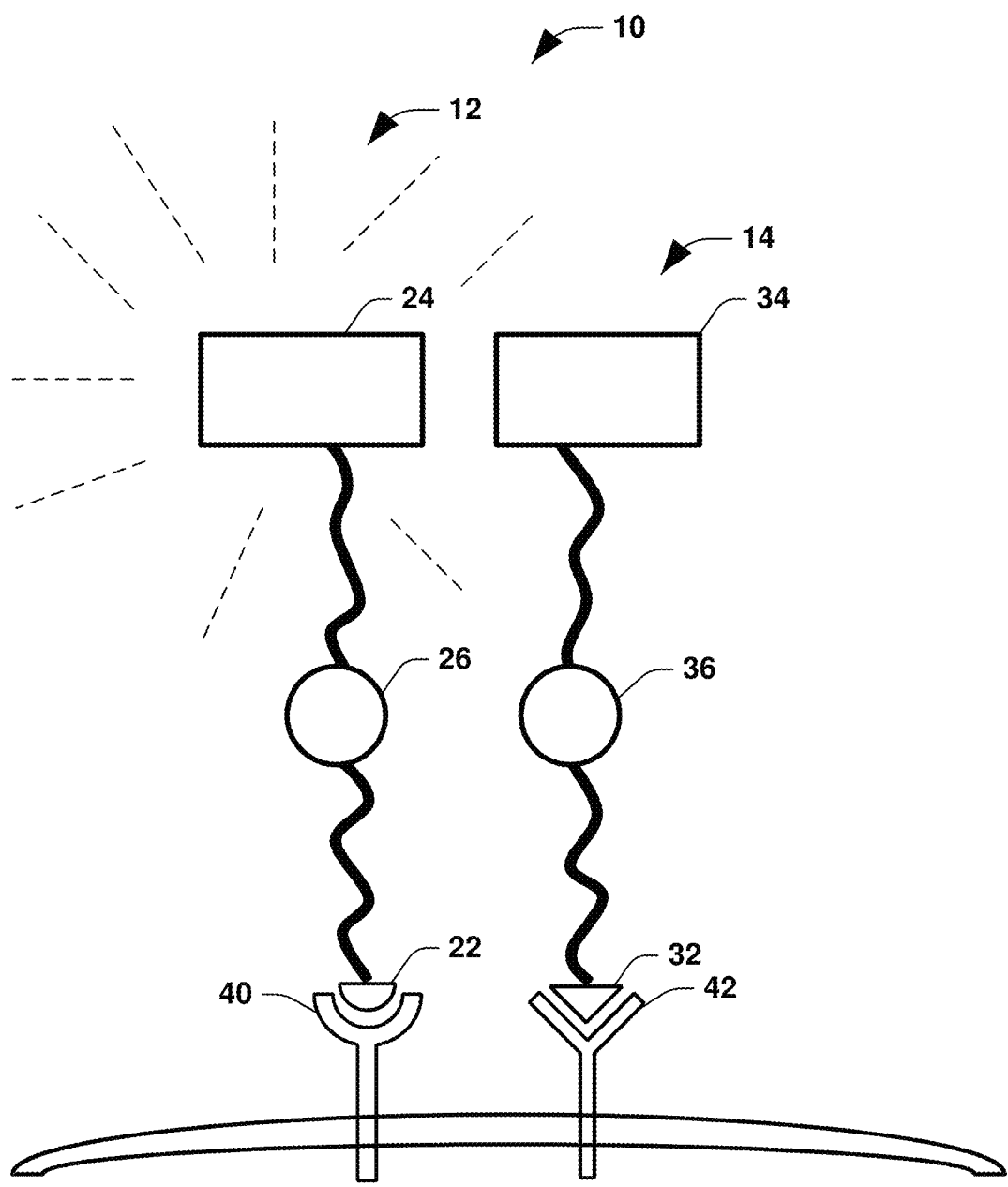
FIG. 1 is a schematic illustration of a first imaging probe and a second imaging probe in accordance with an aspect of the application.

All scientific and technical terms used in this application have meanings commonly used in the art unless otherwise specified. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

In the context of the application, the term "sample" can refer to a specimen or culture obtained from any source, as well as clinical, research, biological and environmental samples. Biological samples may be obtained from animals (including humans) and encompass cells, fluids, solids, tissues, and organs, and whole organisms.

As used herein, the term "subject" can refer to any animal including, but not limited to, humans and non-human animals (e.g., rodents, arthropods, insects, fish (e.g., zebrafish)), non-human primates, ovines, bovines, ruminants, lagomorphs, porcines, caprines, equines, or canines felines, ayes, etc.).

As used herein, the terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

As used herein, the terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, meningoma, medulloblastoma, schwannoma and epidymoma.

As used herein, the term "polynucleotide" can refer to oligonucleotides, nucleotides, or to a fragment of any of these, to DNA or RNA (e.g., mRNA, rRNA, tRNA) of genomic or synthetic origin, which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids, i.e., oligonucleotides, containing known analogues of natural nucleotides. The term can also encompass nucleic acid-like structures with synthetic backbones.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term can also include peptides and polypeptide fragments, motifs and the like, glycosylated polypeptides, and all "mimetic" and "peptidomimetic" polypeptide forms.

As used herein, the term "small molecule" can refer to lipids, carbohydrates, polynucleotides, polypeptides, or any other organic or inorganic molecules.

As used herein, the term "imaging probe" can refer to a biological moiety that may be used to detect, image, and/or monitor the presence and/or progression of a cell cycle, cell function/physiology, condition, pathological disorder and/or disease.

As used herein, the terms "treating" or "treatment" of a disease can refer to executing a treatment protocol to eradicate at least one diseased cell. Thus, "treating" or "treatment" does not require complete eradication of diseased cells.

As used herein, the term "diagnostically effective amount" can refer to an amount of an imaging composition that is sufficient to enable imaging of at least one cell, tissue, or organism using an imaging modality.

As used herein, the term "targeting moiety" can refer to a molecule or molecules that are able to bind to and complex with a biomarker. The term can also refer to a functional group that serves to target or direct an imaging probe to a particular location, cell type, diseased tissue, or association. In general, a "targeting moiety" can be directed against a biomarker.

As used herein, the term "molecular signature" can refer to a unique expression pattern of one or more biomarkers (e.g., gene(s) or protein(s)) of a cell.

As used herein, the term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class.

As used herein, the term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

As used herein, the term "diabodies" refers to dimeric scFvs. The components of diabodies typically have shorter peptide linkers than most scFvs and they show a preference for associating as dimers.

As used herein, the term "epitope" refers to a physical structure on a molecule that interacts with a selective component. In exemplary embodiments, epitope refers to a desired region on a target molecule that specifically interacts with a selectivity component.

As used herein, the term "Fab" refers to an antibody fragment that is essentially equivalent to that obtained by digestion of immunoglobulin (typically IgG) with the enzyme papain. The heavy chain segment of the Fab fragment is the Fd piece. Such fragments may be enzymatically or chemically produced by fragmentation of an intact antibody, recombinantly produced from a gene encoding the partial antibody sequence, or it may be wholly or partially synthetically produced.

As used herein, the term "Fab'" refers to an antibody fragment that is essentially equivalent to that obtained by reduction of the disulfide bridge or bridges joining the two heavy chain pieces in the F(ab')$_2$ fragment. Such fragments may be enzymatically or chemically produced by fragmentation of an intact antibody, recombinantly produced from a gene encoding the partial antibody sequence, or it may be wholly or partially synthetically produced.

As used herein, the term "F(ab')$_2$" refers to an antibody fragment that is essentially equivalent to a fragment obtained by digestion of an immunoglobulin (typically IgG) with the enzyme pepsin at pH 4.0-4.5. Such fragments may be enzymatically or chemically produced by fragmentation of an intact antibody, recombinantly produced from a gene encoding the partial antibody sequence, or it may be wholly or partially synthetically produced.

As used herein, the term "Fv" refers to an antibody fragment that consists of one $V_H$ and one $V_L$ domain held together by noncovalent interactions. The term "dsFv" is used herein to refer to an Fv with an engineered intermolecular disulfide bond to stabilize the $V_H$-$V_L$ pair.

As used herein, the term "immunogen" traditionally refers to compounds that are used to elicit an immune response in an animal, and is used as such herein. However, many techniques used to produce a desired selectivity component, such as the phage display and aptamer methods described below, do not rely wholly, or even in part, on animal immunizations. Nevertheless, these methods use compounds containing an "epitope," as defined above, to select for and clonally expand a population of selectivity components specific to the "epitope." These in vitro methods mimic the selection and clonal expansion of immune cells in vivo, and, therefore, the compounds containing the "epitope" that is used to clonally expand a desired population of phage, aptamers and the like in vitro are embraced within the definition of "immunogens."

As used herein, the terms "single-chain Fvs" and "scFvs" refers to recombinant antibody fragments consisting of only the variable light chain ($V_L$) and variable heavy chain ($V_H$) covalently connected to one another by a polypeptide linker. Either $V_L$ or $V_H$ may be the NH$_2$-terminal domain. The polypeptide linker may be of variable length and composition so long as the two variable domains are bridged without serious steric interference. In exemplary embodiments, the linkers are comprised primarily of stretches of glycine and serine residues with some glutamic acid or lysine residues interspersed for solubility.

This application generally relates to compositions and methods for imaging cells, and more particularly to imaging probes for ex vivo or in vivo determination of a cell's molecular signature. The compositions and methods described herein can provide a biomarker pattern-recognition paradigm that may allow visualization of biochemical processes and/or dynamic biomarker expression levels. Detection of different molecular signatures by the compositions and methods of the application can transform molecular imaging from single biomarker identification to imaging and interrogating cellular dynamics during complex processes, such as embryonic development, growth and proliferation, apoptosis, and necrosis, as well as cellular changes that occur in the course of diseases or disorders. The compositions and methods described herein can decrease background imaging artifacts, increase diagnostic specificity, promote the ability to interrogate the status of cells rather than just the presence of a biomarker, and determine the type, stage, and/or severity of one or more diseases or disorders, such as cancer, inflammatory disorders, or ischemia.

One aspect of the application relates to an imaging composition for imaging a cell having a first biomarker and a second biomarker that is different than the first biomarker. Referring to FIG. 1, the imaging composition 10 can include a first imaging probe 12 and a second imaging probe 14. The first imaging probe 12 can include a first targeting moiety 22 that is linked to a first reporter moiety 24 via a linker region 26. The second imaging probe 14 can include a second targeting moiety 32, which is different than the first targeting moiety 22 and is linked to a second reporter moiety 34 via a linker region 36. The first and second targeting moieties 22 and 32 can specifically complex with the first and second biomarkers 40 and 42, respectively. As described in more detail below, the first reporter moiety 24 and the second reporter moiety 34 can form a signaling complex and thereby produce a detectable signal when the first and second imaging probes 12 and 14 complex with first and second biomarkers 40 and 42 that are proximate (e.g., in spatial proximity) to one another. Advantageously, the first reporter moiety 24 and the second reporter moiety 34 do not produce a detectable signal when the first and second imaging probes 12 and 14 do not complex with the first and second biomarkers 40 and 42 of the cells, such as when the first imaging probe 12 and second imaging probe are in solution, or do not complex with first and second biomarkers 40 and 42 of the cell that are not proximate to one another. The imaging composition 10, as described below, can be used for in vivo or ex vivo diagnostic and/or research purposes (e.g., drug screening applications).

In some embodiments, the targeting moieties can comprise any molecule, or complex of molecules, which is/are capable of interacting with an intracellular, cell surface, or extracellular biomarker of the cell. The biomarker can include, for example, a cellular protease, a kinase, a protein, a cell surface receptor, a lipid, and/or fatty acid. In one example, the cellular protease, kinase, protein, cell surface receptor, lipid, and/or fatty acid can change in expression at the cell surface as the cell becomes apoptotic. Other examples of biomarkers that the targeting moieties can interact with include molecules associated with a particular disease. For example, the biomarkers can include cell surface receptors implicated in cancer development, such as epidermal growth factor receptor and transferrin receptor. The targeting moieties can interact with the biomarkers through non-covalent binding, covalent binding, hydrogen binding, van der Waals forces, ionic bonds, hydrophobic interactions, electrostatic interaction, and/or combinations thereof.

The targeting moieties can include, but are not limited to, synthetic compounds, natural compounds or products, macromolecular entities, bioengineered molecules (e.g., polypeptides, lipids, polynucleotides, antibodies, antibody fragments), and small entities (e.g., small molecules, neurotransmitters, substrates, ligands, hormones and elemental compounds).

In one example, the first and/or second targeting moiety can comprise an antibody, such as a monoclonal antibody, a polyclonal antibody, or a humanized antibody. including without limitation: Fv fragments, single chain Fv (scFv) fragments, Fab' fragments, F(ab')$_2$ fragments, single domain antibodies, camelized antibodies and antibody fragments, humanized antibodies and antibody fragments, and multivalent versions of the foregoing; multivalent targeting moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

Preparation of antibodies may be accomplished by any number of well-known methods for generating monoclonal antibodies. These methods typically include the step of immunization of animals, typically mice, with a desired immunogen (e.g., a desired target molecule or fragment thereof). Once the mice have been immunized, and preferably boosted one or more times with the desired immunogen(s), monoclonal antibody-producing hybridomas may be prepared and screened according to well known methods. See, for example, Kuby, Janis, Immunology, Third Edition, pp. 131-139, W. H. Freeman & Co. (1997), for a general overview of monoclonal antibody production, that portion of which is incorporated herein by reference.

Over the past several decades, antibody production has become extremely robust. In vitro methods that combine antibody recognition and phage display techniques allow one to amplify and select antibodies with very specific binding capabilities. See, for example, Holt, L. J. et al., "The Use of Recombinant Antibodies in Proteomics," Current Opinion in Biotechnology, 2000, 11:445-449, incorporated herein by reference. These methods typically are much less cumbersome than preparation of hybridomas by traditional monoclonal antibody preparation methods. Binding epitopes may range in size from small organic compounds such as bromo uridine and phosphotyosine to oligopeptides on the order of 7-9 amino acids in length.

In one embodiment, phage display technology may be used to generate a targeting moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as a Fab' fragment, may be cloned into phage display vectors for surface expression on phage particles. The phage may be any phage, such as lambda, but typically is a filamentous phage, such as Fd and M13, typically M13.

In phage display vectors, the $V_H$-linker-$V_L$ sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacterial cells is the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction, and screening methods are described in detail in, among others, U.S. Pat. Nos. 5,702,892, 5,750,373, 5,821,047 and 6,127,132, each of which are incorporated herein by reference in their entirety.

The targeting moiety need not originate from a biological source. The targeting moiety may, for example, be screened from a combinatorial library of synthetic peptides. One such method is described in U.S. Pat. No. 5,948,635, incorporated herein by reference, which described the production of phagemid libraries having random amino acid insertions in the pIII gene of M13. These phage may be clonally amplified by affinity selection as described above.

The immunogens used to prepare targeting moieties having a desired specificity will generally be the target molecule, or a fragment or derivative thereof. Such immunogens may be isolated from a source where they are naturally occurring or may be synthesized using methods known in the art. For example, peptide chains may be synthesized by 1-ethyl-3-[dimethylaminoproply]carbodiimide (EDC)-catalyzed condensation of amine and carboxyl groups. In certain embodiments, the immunogen may be linked to a carrier bead or protein. For example, the carrier may be a functionalized bead such as SASRIN resin commercially available from Bachem, King of Prussia, Pa. or a protein such as keyhole limpet hemocyanin (KLH) or bovine serum albumin (BSA). The immunogen may be attached directly to the carrier or may be associated with the carrier via a linker, such as a non-immunogenic synthetic linker (for example, a polyethylene glycol (PEG) residue, amino caproic acid or derivatives thereof) or a random, or semi-random polypeptide.

In certain embodiments, it may be desirable to mutate the binding region of the polypeptide targeting moiety and select for a targeting moiety with superior binding characteristics as compared to the un-mutated targeting moiety. This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the targeting moieties may be modified to make them more resistant to cleavage by proteases. For example, the stability of targeting moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting moiety may be of the D configuration. The switch from L to D amino acids neutralizes the digestion capabilities of many of the ubiquitous peptidases found in the digestive tract. Alternatively, enhanced stability of a targeting moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a targeting moiety may be achieved by intercalating one or more dextrorotatory amino acids (such as, dextrorotatory phenylalanine or dextrorotatory tryptophan) between the amino acids of targeting moiety. In exemplary embodiments, such modifications increase the protease resistance of a targeting moiety without affecting the activity or specificity of the interaction with a desired target molecule.

In certain embodiments, the antibodies or variants thereof may be modified to make them less immunogenic when administered to a subject. For example, if the subject is human, the antibody may be "humanized"; where the complimentarily determining region(s) of the hybridoma-derived antibody has been transplanted into a human monoclonal antibody, for example as described in Jones, P. et al. (1986), Nature, 321, 522-525 or Tempest et al. (1991), Biotechnology, 9, 266-273. Also, transgenic mice, or other mammals, may be used to express humanized antibodies. Such humanization may be partial or complete.

In certain embodiments, a targeting moiety as described herein may comprise a homing peptide, which selectively directs the first imaging probe and/or the second imaging probe to a targeted cell. Homing peptides for a targeted cell can be identified using various methods well known in the art. Many laboratories have identified the homing peptides that are selective for cells of the vasculature of brain, kidney, lung, skin, pancreas, intestine, uterus, adrenal gland, retina, muscle, prostate, or tumors. See, for example, Samoylova et al., 1999, Muscle Nerve, 22:460; Pasqualini et al., 1996 Nature, 380:364; Koivunen et al., 1995, Biotechnology, 13:265; Pasqualini et al., 1995, J. Cell Biol., 130:1189; Pasqualini et al., 1996, Mole. Psych., 1:421, 423; Rajotte et al., 1998, J. Clin. Invest., 102:430; Rajotte et al., 1999, J. Biol. Chem., 274:11593. See, also, U.S. Pat. Nos. 5,622, 6999; 6,068,829; 6,174,687; 6,180,084; 6,232,287; 6,296, 832; 6,303,573; and 6,306,365.

Phage display technology provides a means for expressing a diverse population of random or selectively randomized peptides. Various methods of phage display and methods for producing diverse populations of peptides are well known in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed, are also described in Smith et al., 1993, Meth. Enzymol., 217:228-257, Scott et al., Science, 249:386-390, and two PCT publications WO 91/07141 and WO 91/07149. Phage display technology can be particularly powerful when used, for example, with a codon based mutagenesis method, which can be used to produce random peptides or randomly or desirably biased peptides (see, e.g., U.S. Pat. No. 5,264,563). These or other well-known methods can be used to produce a phage display library, which can be subjected to the in vivo phage display method in order to identify a peptide that homes to one or a few selected tissues.

In vitro screening of phage libraries has previously been used to identify peptides that bind to antibodies or cell surface receptors (see, e.g., Smith, et al., 1993, Meth. Enzymol., 217:228-257). For example, in vitro screening of phage peptide display libraries has been used to identify novel peptides that specifically bind to integrin adhesion receptors (see, e.g., Koivunen et al., 1994, J. Cell Biol. 124:373-380), and to the human urokinase receptor (Goodson, et al., 1994, Proc. Natl. Acad. Sci., USA 91:7129-7133).

In certain embodiments, the targeting moiety may comprise a receptor molecule, including, for example, receptors, which naturally recognize a specific desired molecule of a target cell. Such receptor molecules include receptors that have been modified to increase their specificity of interaction with a target molecule, receptors that have been modified to interact with a desired target molecule not naturally recognized by the receptor, and fragments of such receptors (see, e.g., Skerra, 2000, J. Molecular Recognition, 13:167-187). A preferred receptor is a chemokine receptor. Exemplary chemokine receptors have been described in, for example, Lapidot et al, 2002, Exp Hematol, 30:973-81 and Onuffer et al, 2002, Trends Pharmacol Sci, 23:459-67.

In other embodiments, the targeting moiety may comprise a ligand molecule, including, for example, ligands which naturally recognize a specific desired receptor of a target cell. Such ligand molecules include ligands that have been modified to increase their specificity of interaction with a target receptor, ligands that have been modified to interact with a desired receptor not naturally recognized by the ligand, and fragments of such ligands.

In still other embodiments, the targeting moiety may comprise an aptamer. Aptamers are oligonucleotides that are selected to bind specifically to a desired molecular structure of the target cell. Aptamers typically are the products of an affinity selection process similar to the affinity selection of phage display (also known as in vitro molecular evolution). The process involves performing several tandem iterations of affinity separation, e.g., using a solid support to which the diseased immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids (PNAs) and phosphorothioate nucleic acids.

In yet other embodiments, the targeting moiety may be a peptidomimetic. By employing, for example, scanning mutagenesis to map the amino acid residues of a protein, which is involved in binding other proteins, peptidomimetic compounds can be generated which mimic those residues which facilitate the interaction. Such mimetics may then be used as a targeting moiety to deliver the first imaging probe and/or second imaging probe to a target cell. For instance, non-hydrolyzable peptide analogs of such resides can be generated using benzodiazepine (e.g., see Freidinger et al. in Peptides: Chemisty and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al., 1986, J Med Chem 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., 1985, Tetrahedron Lett 26:647; and Sato et al., 1986, J Chem Soc Perkin Trans 1:1231), and β-aminoalcohols (Gordon et al., 1985, Biochem Biophys Res Cummun 126:419; and Dann et al., 1986, Biochem Biophys Res Commun 134:71).

By way of example, where the cell targeted comprises a cancer cell, the first targeting moiety can comprise an antibody to human extracellular growth factor receptor (EGFR) and the second targeting moiety can comprise an antibody to human transferrin receptor (TfR). Overexpression of EGFR and TfR has been implicated in the malignant phenotype of tumor cells. Tumors that overexpress EGFR and TfR have increased activity that leads to uncontrolled cell growth accompanied by decreased apoptosis and increased angiogenesis. The overexpression of these receptors also leads to activation of other genes that promote cancer growth through such means as invasion and metastasis, as well as resistance to chemotherapy and radiotherapy. The imaging of cancer cells expressing EGFR and TfR can provide a molecular signature of the malignancy or progression of such cells.

In some embodiments, the linker regions of the first and second imaging probes can be the same or different. Additionally, one or both of the first and second imaging probes can include two or more linker regions. The linker can be of any suitable length and contain any suitable number of atoms and/or subunits. Advantageously, the linker region is sufficiently flexible so that the first reporter moiety and the second reporter moiety can interact with one another when the first and second imaging probes complex respectively with that first biomarker and the second biomarker.

The linker region can comprise one or combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof. In one example of the application, the linker region can comprise a streptavidin linkage. The streptavidin linkage can be attached to a targeting moiety (e.g. first targeting moiety or second targeting moiety) and reporter moiety (e.g., first reporter moiety or second reporter moieties) via biotin attachment groups that are coupled respectively to the targeting moiety and reporter moiety.

The first reporter moiety linked to the first targeting moiety by the linker region is different from the second reporter moiety linked to the second targeting moiety. The first reporter moiety can include any molecule or complex of molecules capable of interacting with at a least one second reporter moiety to form a signaling complex in order to effect the potential for a detectable signal. Advantageously, the first reporter moiety and the second reporter moiety only produce a detectable signal when the first imaging probe and the second imaging probe complex, respectively, with the first biomarker and the second biomarker.

Examples of molecules that can potentially be used as the first reporter moiety and/or second reporter moiety include isotopic labels, such as a naturally non-abundant heavy isotope or radioactive isotope; optically detectable moieties, such as a chromophore, luminophore, fluorophore, quantum dot or nanoparticle light scattering label; electromagnetic spin label; calorimetric agent; magnetic substance; electron-rich material such as a metal; electrochemiluminescent label; moiety that can be detected based on a nuclear magnetic, paramagnetic, electrical, charge to mass, or thermal characteristic; light scattering or plasmon resonant materials, such as gold or silver particles; or multielement reporter systems, such as affinity tags including but not limited to enzyme and substrate reporter groups, and dinitrophenyl (DNP) reporter group and fluorophore labeled anti-DNP antibody and the like. Fluorophores that can potentially be used include, for example, fluorescent lanthanide complexes, including those of Europium and Terbium, fluorescein, fluorescein isothiocyanate, dichlorotriazinylamine fluorescein, rhodamine, tetramethylrhodamine, umbelliferone, eosin, erythrosin, coumarin, methyl-coumarins, pyrene, Malacite green, Cy3, Cy5, stilbene, Lucifer Yellow, Cascade Blue, Texas Red, alexa dyes, dansyl chloride, phycoerythin, luciferin, green fluorescent protein and its wavelength shifted variants, bodipy, and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), or WO 98/59066.

In some embodiments, the first reporter moiety can include an imaging agent and the second reporter moiety can include an activator molecule capable of interacting with the imaging agent to form a signaling complex in order to effect the potential for a detectable signal. Upon interaction with the activator molecule and forming the signaling complex, the imaging agent, a portion of the imaging agent, and/or a reaction byproduct of the interaction can produce a detectable signal. As described in more detail below, the signal generated by formation of the signaling complex can be detected using one or a combination of imaging modalities, such as optical, nuclear, and magnetic resonance techniques.

In some aspects of the application, the imaging agent can be cloaked with a substrate that is wholly or partially susceptible to enzymatic cleavage (e.g., sugarases) by the activator molecule when the first imaging probe and second imaging probe complex respectively with the first biomarker and the second biomarker. The activator molecule can include an enzyme that produces a detectable product upon interaction with the imaging agent. Examples of such enzymes include but are not limited to horseradish peroxidase, alkaline phosphatase, β-galactosidase, luciferase, or acetylcholinesterase, β-lactamase, alpha-secretases, and matrix metalloproteinases (e.g., MMP 11).

In another aspect of the application, the imaging agent can include a metal-ion chelator, which coordinates a paramagnetic ion. The metal-ion chelator can be cloaked with a substrate that is wholly or partially susceptible to enzymatic cleavage (e.g., sugarases) by the activator molecule when the first imaging probe and second imaging probe complex respectively with the first biomarker and the second biomarker. In some examples, the paramagnetic metal ion can include Gd(III), Fe(III), Mn(III), Y(III), Cr(III), Eu(III), Tb(III), and/or Dy(III). By way of example, the cloaked enzyme-activated contrast agent can include o-nitrophenyl-b-D-galactopyraniside (ONPG) or its para analog (i.e., PNPG), GB137 or 1-(2-(β-Galactopyranosyloxy)propyl)-4,7,10-tris(carboxymethyl)-1,4,7,10-tetraazacyclododecane) gadolinium(III) (EGadMe).

In some embodiments, the imaging agent can include a self-immolative contrast agent (SICA). The SICA can have a metal-ion chelator connected to an enzyme substrate via a self-immolative linker. The SICA is wholly or partially susceptible to enzymatic cleavage (e.g., sugarases) by the activator molecule when the first imaging probe and second imaging probe complex respectively with the first biomarker and the second biomarker. The first imaging probe having a SICA imaging agent further includes a linker region that links the SICA to the first biomarker. After cleavage by an activator molecule of the second imaging agent, the SICA remains attached via the linker region to the first biomarker. The SICA may be conjugated to a biotin attachment molecule that is capable of coupling the SICA to a streptavidin or avidin linking group. After cleavage by an activator molecule, the SICA remains bound to the linker region via the biotin attachment molecule.

In one example, the first reporter moiety can include a β galactosidase activated magnetic resonance SICA conjugated to a biotin attachment molecule and having the Formula I:

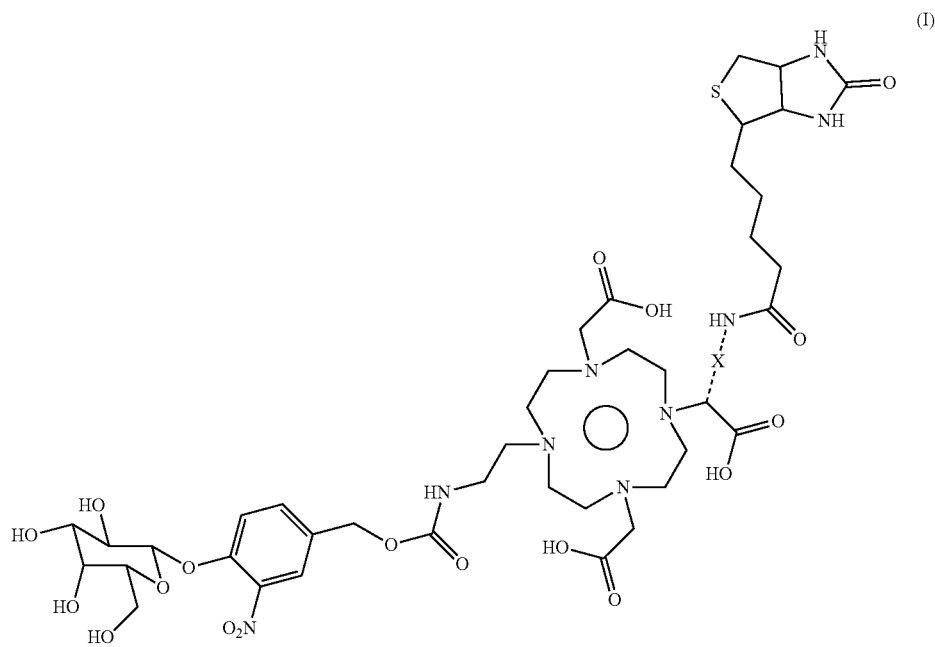

wherein the coordinate metal ion (indicated by the circle) can include Gd(III), Fe(III), Mn(III), Y(III), Cr(III), Eu(III), Tb(III), and/or Dy(III), and X is an optional linker, such as an aliphatic and/or aromatic group.

In another example, the first reporter moiety can include a β galactosidase activated magnetic resonance SICA conjugated to a biotin attachment molecule and having the Formula II:

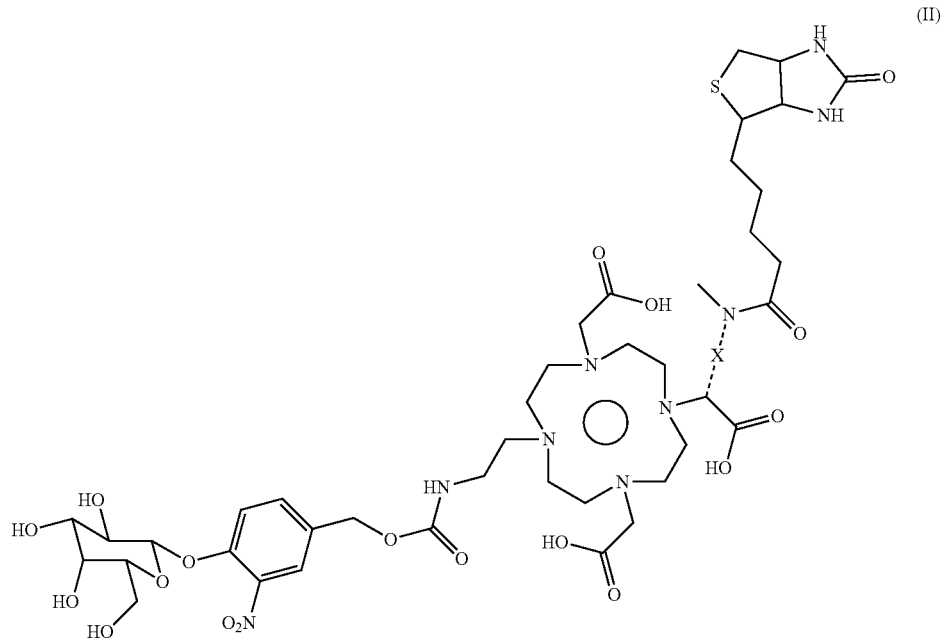

wherein the coordinate metal ion (indicated by the circle) can include Gd(III), Fe(III), Mn(III), Y(III), Cr(III), Eu(III), Tb(III), and/or Dy(III), and X is an optional linker, such as an aliphatic and/or aromatic group.

In another example, the first reporter moiety can include a β galactosidase activated magnetic resonance SICA conjugated to a biotin attachment molecule and having the Formula III:

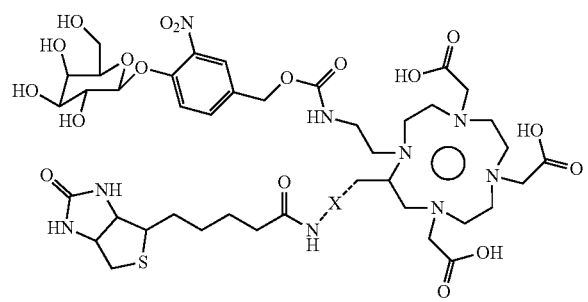

wherein the coordinate metal ion (indicated by the circle) can include Gd(III), Fe(III), Mn(III), Y(III), Cr(III), Eu(III), Tb(III), and/or Dy(III), and X is an optional linker, such as an aliphatic and/or aromatic group.

In yet another example, the first reporter moiety can include a β galactosidase activated magnetic resonance SICA conjugated to a biotin attachment molecule and having the Formula IV:

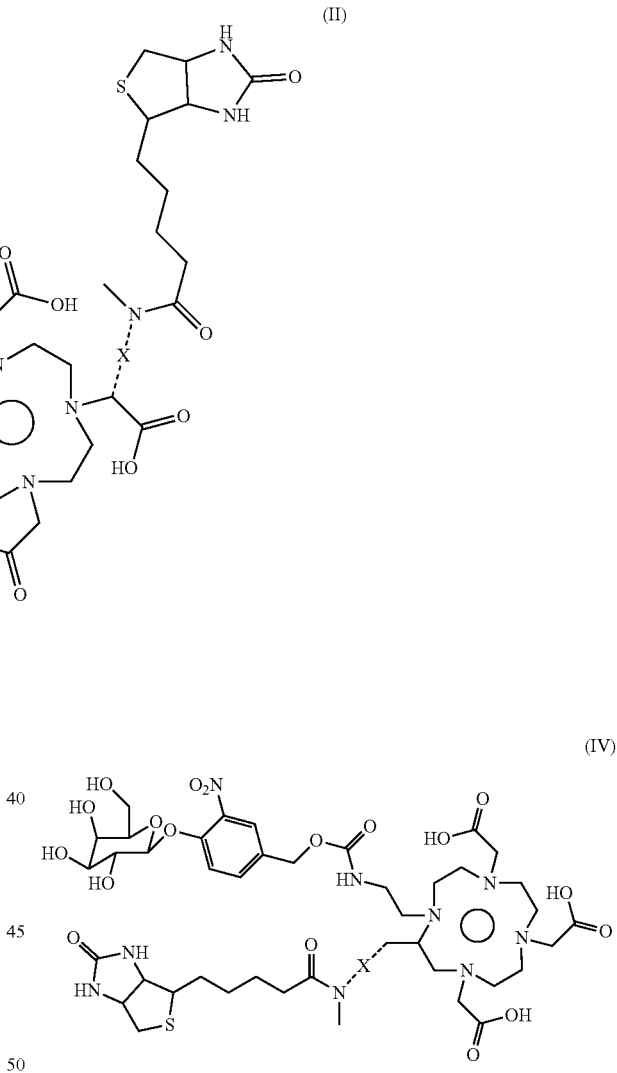

wherein the coordinate metal ion (indicated by the circle) can include Gd(III), Fe(III), Mn(III), Y(III), Cr(III), Eu(III), Tb(III), and/or Dy(III), and X is an optional linker, such as an aliphatic and/or aromatic group.

Figure 2:
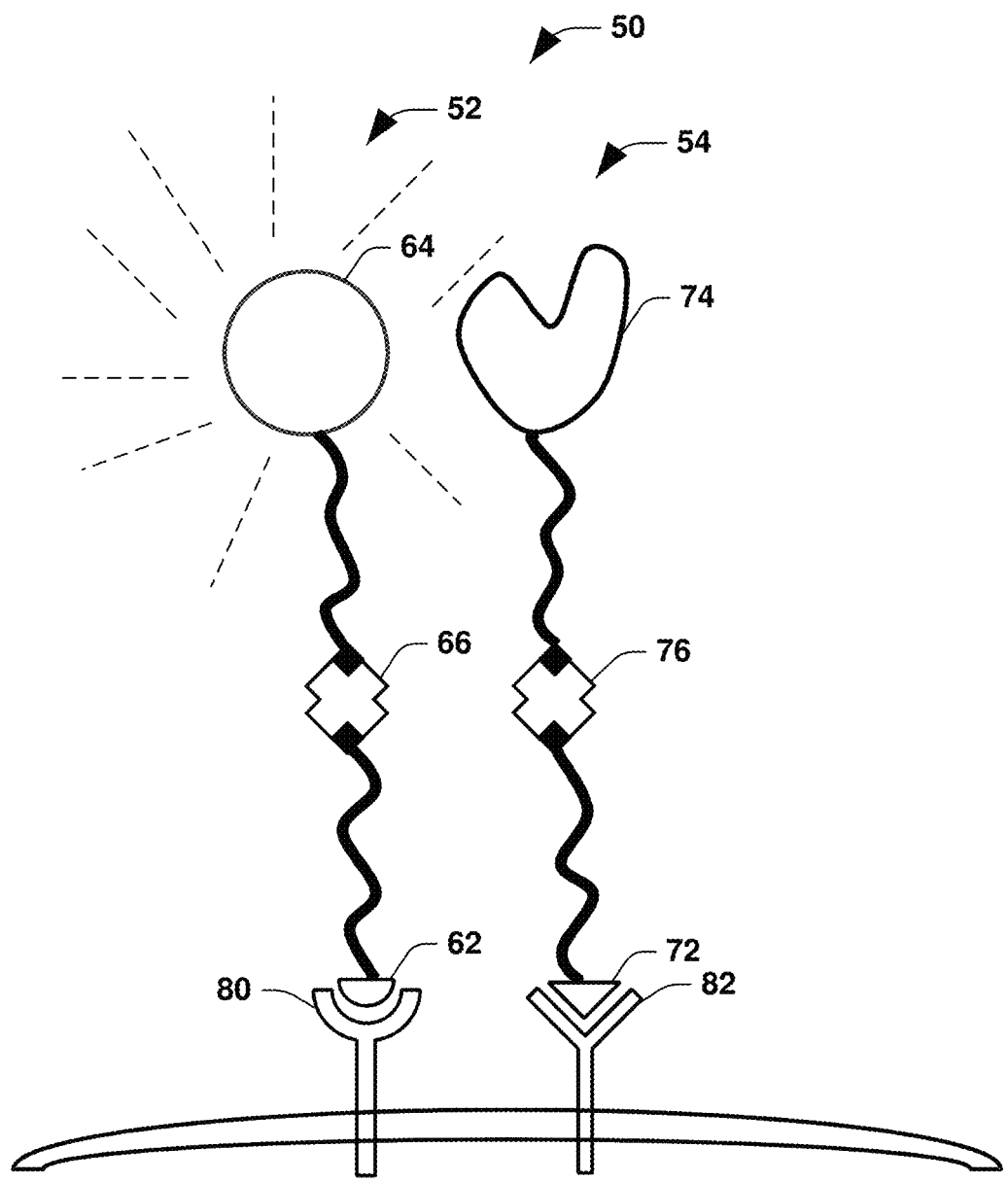
FIG. 2 illustrates a first imaging probe and a second imaging probe in accordance with another aspect of the application.

An example of an imaging composition for imaging a cell having a first biomarker and a second biomarker that is different than the first biomarker is illustrated in FIG. 2. Referring to FIG. 2, the imaging composition 50 can include a first imaging probe 52 and a second imaging probe 54. The first imaging probe 52 can include a first targeting moiety 62 that is linked to a first reporter moiety 64 via a linker region 66. The first reporter moiety 64 can comprise an EGadMe SICA that is attached to a streptavidin linker with biotin. The first targeting moiety 62 is attached to the streptavidin linker 66 with biotin. The second imaging linker 66 can include a second targeting moiety 72, which is different than the first targeting moiety 62 and is linked to a second reporter moiety 74 via a linker region 76. The second reporter moiety 74 can comprise β-galactosidase that is attached to a streptavidin linker 76 with biotin. The second targeting moiety 72 is attached to the streptavidin linker 76 with biotin. Upon complexing of the first and second imaging probes 52 and 54 with first and second biomarkers 80 and 82, respectively, of the target cell, the β-galactosidase of the second reporter moiety 74 can interact with the EGadMe of the first reporter moiety 64 and cleave the cloaking substrate of the EGadMe. Once cleaved, the EGadMe can form a signaling complex and thereby produce a detectable signal upon magnetic resonance.

It will be appreciated that the imaging composition of the application need not be limited to a first imaging probe and a second imaging probe that can complex with a first biomarker and second biomarker of a cell. The imaging composition can also include at least at least three, four, or more imaging probes that complex respectively with three, four, or more different biomarkers of a cell. Each imaging probe can include a reporter moiety that upon interaction with the other reporter moieties, when the at least three imaging probes complex with the at least three biomarkers, form a signaling complex and produce a detectable signal. The use of at least three imaging probes that complex with respectively at three distinct biomarkers allows greater specificity in identifying and imaging cells.

Figure 3:
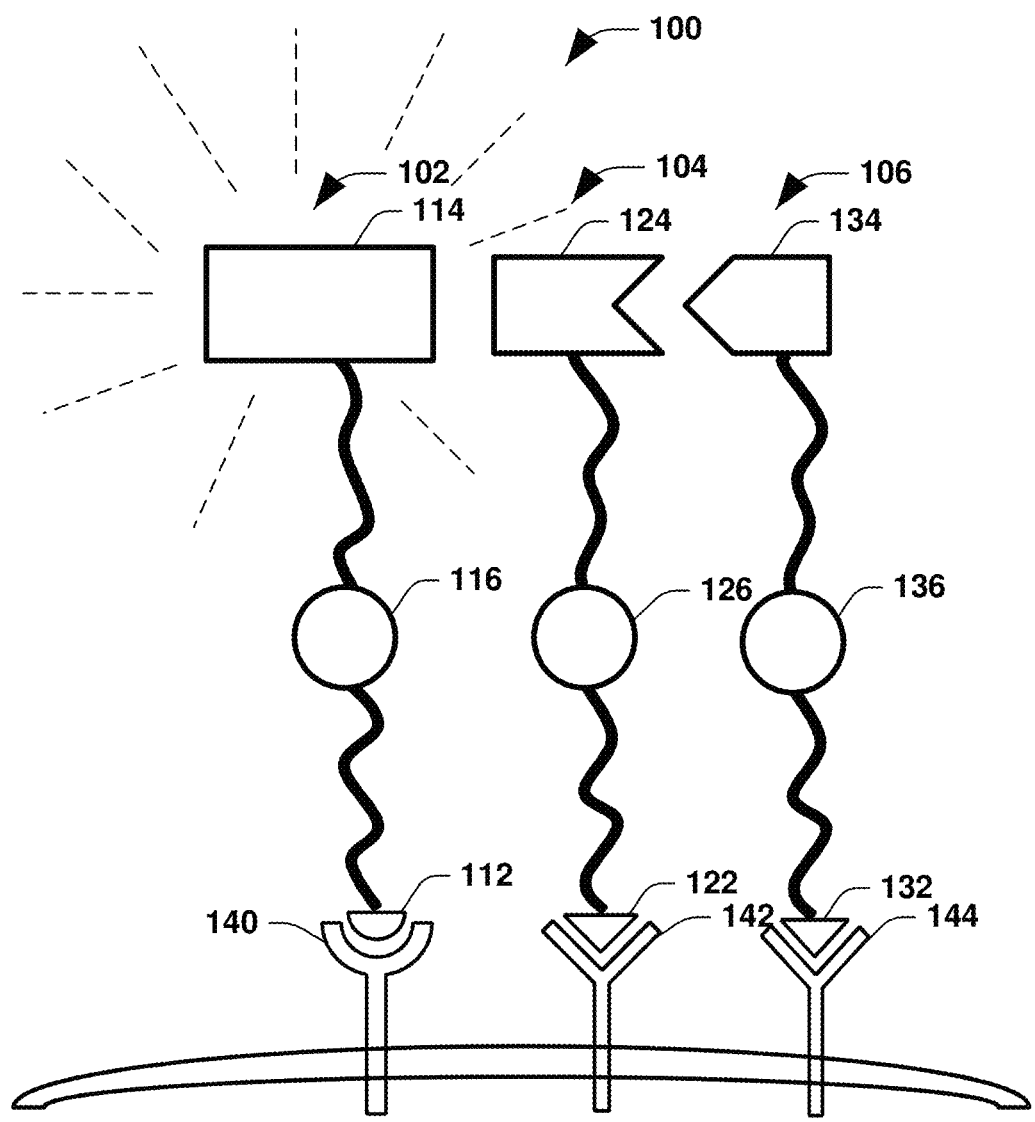
FIG. 3 illustrates a first imaging probe, a second imaging probe, and a third imaging probe in accordance with another aspect of the application.

By way of example, FIG. 3 illustrates an imaging composition 100 for imaging a cell that includes a first biomarker, a second biomarker, and a third biomarker, wherein each biomarker is different than the others. The imaging composition 100 can include a first imaging probe 102, a second imaging probe 104, and a third imaging probe 106. The first imaging probe 102 can include a first targeting moiety 112 that is linked to a first reporter moiety 114 via a linker region 116. The first reporter moiety 114 can include an imaging agent, such as EGadMe. The second imaging probe 104 can include a second targeting moiety 122, which is different than the first targeting moiety 112 and is linked to a second reporter moiety 124 via a linker region 126. The third imaging probe 106 can include a third targeting moiety 132, which is different than the first targeting moiety 112 and the second targeting moiety 122 and is linked to a third reporter moiety 134 via a linker region 136. The first, second, and third targeting moieties 112, 122, and 132 can specifically complex, respectively, with the first, second, and third biomarkers 140, 142, and 144.

The second reporter moiety 124 and the third reporter moiety 134 can include, respectively, split activator molecules, such as split enzymes, which in their split configuration lack activity, e.g., enzymatic activity. The split activator molecules when proximate each other are capable of forming an activator complex, such as a whole enzyme with enzymatic activity, that can interact with the imaging agent of the first reporter moiety 114 when the first, second, and third imaging probes 102, 104, and 106 complex respectively with first, second, and third biomarkers 140, 142, and 144 of a target cell. Interaction of the activator complex of the second reporter moiety 124 and third reporter moiety 134 with first reporter moiety 114 can form a signaling complex that can effect the potential for a detectable signal. Advantageously, the first reporter moiety 114, the second reporter moiety 124, and third reporter moiety 134 do not produce a detectable signal when the first, second, and third imaging probes 102, 104, and 106 do not complex with the first, second, and third biomarkers 140, 142, and 144 of the target cell or do not complex with first, second, and third biomarkers 140, 142, and 144 of the target cell that are not proximate to one another.

In one example, the split activator molecule can comprise a portion of a β-galactosidase molecule that does not possess enzymatic activity alone but when combined with and/or interacts with another portion of a β-galactosidase molecule possesses enzymatic activity. The active β-galactosidase molecule is homo-tetrameric, with each monomer consisting of a polypeptide chain that is 1023 amino acids in length. The polypeptide chain is arranged into an extended N-terminal region and 5 folded domains. As discussed below, mutations truncating or deleting regions of the monomers have the ability to complement and restore enzyme activity in vivo and in vitro. For example, the N-terminal 50 amino acids (i.e., the α peptide) restores activity to acceptor molecules lacking this region (a complementation). Additionally, domain 5 (i.e., the C-terminal domain) also has the ability to restore activity to molecules lacking that region (ω complementation). Thus, the activator molecule can comprise a portion of a β-galactosidase molecule.

In another aspect of the present invention, the first and second imaging probes can be formulated as pharmaceutical compositions. Formulation of pharmaceutical composition for use in the modes of administration noted below (and others) are described, for example, in *Remington's Pharmaceutical Sciences* (18$^{th}$ edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

For example, pharmaceutical compositions of the present application can contain can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxmethylpropylcellulose, lanolin, methylcellulose, petrolatum, polyethylene glycol, polyvinyl alcohol, polyvinylpyrrolidone, and carboxymethylcellulose Examples of formulations for parenteral administration can include aqueous solutions of the first and second imaging probes in water-soluble form, for example, water-soluble salts and alkaline solutions. Especially preferred salts are maleate, fumarate, succinate, S,S tartrate, or R,R tartrate. In addition, suspensions of the first and second imaging probes as appropriate oily injection suspensions can be administered. Suitable lipophilic solvents or vehicles can include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, such as sodium carboxymethyl cellulose, sorbitol and/or dextran. Optionally, the suspension may also contain stabilizers.

Formulations for topical administration to the skin include, for example, ointments, creams, gels and pastes comprising the first and second imaging probe in a pharmaceutical acceptable carrier. The formulation of first and second imaging probe for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

The composition comprising the first imaging probe and the second probe can be used in a method for imaging a cell having a first biomarker and a second biomarker that is different than the first biomarker. The cells can comprise a diseased cell or healthy cell that is derived from, or a part of, various tissue types, such as neuronal tissue (including both neuron and glia), connective tissue, hepatic tissue, pancreatic tissue, kidney tissue, bone marrow tissue, cardiac tissue, retinal tissue, intestinal tissue, lung tissue, endothelium tissue, cartilage, skeletal muscle, cardiac muscle, other cardiac tissue that is not muscle, smooth muscle, bone, tendon, ligament, adipose tissue and skin. Depending upon the particular application, the cell may be in vivo or ex vivo. Ex vivo cells can be collected as part of one or more samples using one or a combination of known techniques (e.g., biopsy) and, if needed, further processed (e.g., centrifuged) prior to culture, analysis, etc.

One step of the method can include contacting the cell with a diagnostically effective amount of an imaging composition. Depending upon the particular target cell and/or population of target cells, the particular components of the first and second imaging probes comprising the imaging composition can be varied as discussed above. For example, where the cell is suspected of expressing first and second biomarkers of interest, the imaging composition (i.e., the first and second imaging probes) can only contain first and second targeting moieties that specifically complex with the suspected first and second biomarkers (respectively). Alternatively, where the target cell contains an unknown number and type of biomarkers, the imaging composition can comprise a variety of targeting moieties that specifically complex with a variety of different biomarkers.

The cell can be contacted with the imaging composition either ex vivo or in vivo. To contact the cell with the imaging composition ex vivo, a sample can first be obtained. The sample can be obtained directly from a subject (e.g., a biopsy) or, alternatively, obtained from a frozen or preserved tissue sample. The sample can then be contacted with the imaging composition for a time sufficient to allow the first and second targeting moieties of the first and second imaging probes to respectively complex with first and second biomarkers of the cell (if present). Upon contacting the imaging composition with the cell, one or more imaging modalities can be used to detect a signal that will be generated if the first and second biomarkers are present and in sufficient proximity to one another to allow the first reporter moiety to complex and/or interact with the second reporter moiety. If one or both of the first and second biomarker is not present, however, and/or the first and second biomarkers are not in sufficient spatial proximity to one another, then the first reporter moiety will not complex with the second reporter moiety and, thus, a detectable signal will not be generated.

To contact the cell with the imaging composition in vivo, the diagnostically effective amount of an imaging composition can be administered to a subject. Methods of introduction include, but are not limited to, topical, local, intradermal, intramuscular, intraperitoneal, intravenous, subcutaneous, intranasal, rectal, vaginal, and oral routes. The imaging composition may be administered by any convenient route, such as by infusion or bolus injection or by absorption through epithelial or mucocutaneous linings (e.g., oral mucosa, vaginal, rectal and intestinal mucosa, etc.), and may be administered together with other biologically active agents. The imaging composition may be introduced into the central nervous system by any suitable route, including intraventricular injection, intrathecal injection, or intraventricular injection via an intraventricular catheter that is attached to a reservoir.

The imaging composition can be delivered systematically (e.g., intra-venously), regionally, or locally (e.g., intra- or peri-tumoral injection) by, for example, intra-arterial, intra-tumoral, intra-venous, parenteral, intra-pneural cavity, topical, oral or local administration, as well as subcutaneous, intra-zacheral (e.g., by aerosol), or transmucosal (e.g., voccal, bladder, vaginal, uterine, rectal, nasal, mucosal). If delivery of the imaging composition to the brain is desired, the imaging composition can be injected into an artery of the carotid system of arteries (e.g., occipital artery, auricular artery, temporal artery, cerebral artery, maxillary artery etc.). As discussed above, the imaging composition can be formulated as a pharmaceutical composition for in vivo administration.

The amount of the imaging composition sufficient to provide the desired result(s) will depend on a variety of factors, such as the amount required to avoid undesirable physiological results. The precise dose to be employed can also depend on the route of administration, and should be decided according to the judgment of a medical practitioner and each subject's circumstances. In addition, known in vitro and in vivo assays may optionally be employed to help identify optimal dosage ranges. Effective doses may be extrapolated from dose-response curves derived from in vitro or in vivo test systems.

The imaging composition can be administered in a variety of unit dosage forms, depending upon the particular cell or tissue being imaged, the general medical condition of each subject, the method of administration, and the like. Details on dosages are well described in the scientific literature. The exact amount and concentration of the imaging composition, or the "effective dose", can be routinely determined (e.g., by a medical practitioner). The "dosing regimen" will depend upon a variety of factors, such as whether the cell or tissue to be imaged is disseminated or local, the general state of the subject's health, the subject's age, and the like. Using guidelines describing alternative dosing regimens, e.g., from the use of other imaging agents and compositions, the skilled artisan can readily determine by routine trials the optimal effective concentrations of the imaging composition.

In another aspect, a method is provided for determining a molecular signature of a cell that is associated with a disease. Examples of such diseases can include genetic, skeletal, renal, dental, immunological, vascular or hematological, muscular or connective tissue, neurological, ocular, auditory or vestibular, dermatological, endocrinological, olfactory, cardiovascular, reproductive, urinary, psychological, gastrointestinal, respiratory/pulmonary, neoplastic, or inflammatory medical conditions. Other examples of diseases can include diabetes, cardiovascular disease, amyotrophic lateral sclerosis, Parkinson's disease, Huntington's disease, multiple sclerosis, stroke, myocardial infarction, spinal cord injury, brain injury, peripheral neuropathy, autoimmune diseases, liver-based metabolic diseases, acute liver failure, chronic liver disease, leukemia, sickle-cell anemia, bone defects, muscular dystrophy, burns, osteoarthritis, and macular degeneration. The disease can be the result of one or a combination of etiologies, including vascular, ischemic, thrombotic, embolic, infectious (e.g., bacterial, viral, parasitic, fungal, abscessal), neoplastic, drug-induced, metabolic, immunological, collagenic, traumatic, surgical/iatrogenic, idiopathic, endocrinological, allergic, degenerative, congenital, accelerated apoptosis and abnormal malformational causes. The method can be used to measure or monitor efficacy of a therapeutic agent or modality used to treat the disease.

One step of the method can include contacting the cell with a diagnostically effective amount of an imaging composition. As discussed above, the particular components of the first and second imaging probes comprising the imaging composition can be varied depending upon the particular target cell and/or population of target cells to be imaged. The cell can then be contacted with the imaging composition either ex vivo or in vivo (as discussed above). Upon contacting the imaging composition with the cell, one or more imaging modalities can be used to detect a signal that will be generated if the first and second biomarkers are present and in sufficient proximity to one another to allow the activator moiety to complex with the reporter moiety. If one or both of the first and second biomarker is not present, however, and/or the first and second biomarkers are not in sufficient geometric proximity to one another, then the first reporter moiety will not interact and/or complex with the second reporter moiety and, thus, a detectable signal will not be generated.

The signal(s) detected by the imaging modality (or modalities) can then be used to produce a molecular signature of the cell. Biomarker expression for a given cell can vary both spatially and temporally and, thus, a cell (whether healthy or diseased) has a unique temporal and spatial expression pattern of biomarkers. The molecular signature produced by the present invention, which represents the expression patterns of two or more different cell biomarkers, can be indicative of the type, stage, or severity of the disease.

In one example, the method of the present invention can be used to determine a molecular signature of a cell associated with cancer. The number of amplified biomarkers (e.g., cell surface receptors) is known to increase with cancer stage. Thus, accurately assessing the multi-step progression of cancer growth requires accurate imaging of the coordinated overexpression of multiple cell biomarkers. Based on the produced molecular signature of one or more cancer biomarkers, the present invention can spatially and temporally resolve complex heterogeneous samples to differentially image normal tissues from abnormal tissues and thereby differentiate early stage cancer from more advanced cancer stages. This is unlike conventional cancer imaging modalities and techniques, which typically rely on detection of only one cancer biomarker. Consequently, the method provides at least the following advantages: (1) increased specificity; (2) multi-biomarker imaging at the cellular level; (3) the ability to recognize distinct biomarker patterns among different tumor types and grades; and (4) increased signal to noise.

In another example, the imaging composition of the present invention can be used as part of an intra-operative molecular imaging (IOI) procedure, as disclosed in U.S. patent application Ser. No. 11/811,818 to Basilion, to detect abnormal cells and/or diseased tissue. To identify and facilitate removal of abnormal cells, for example, microscopic IOI techniques can be combined with topically applied imaging compositions of the present invention. Thus, the imaging composition can be delivered via topical injection, as opposed to intravenous injection, which facilitates localized diffusion of the imaging probes. In one example, the imaging composition can be combined with IOI to identify malignant cells that have infiltrated and/or are beginning to infiltrate at a tumor brain margin. The method can be performed in real-time during brain or other surgery. The method can include topical application of an imaging composition comprising a first imaging probe whose targeting moiety specifically complexes with an abnormal cell marker (e.g., protease specific) and a second imaging probe whose targeting moiety can specifically complex with a different cell marker that is in proximity to the abnormal cell marker. An imaging modality can then be used to detect and subsequently gather image data. The resultant image data may be used to determine, at least in part, a radiological treatment. Alternatively, this image data may be used to control, at least in part, an automated surgical device (e.g., laser, scalpel, micromachine) or to aid in manual guidance of surgery. Further, the image data may be used to plan and/or control the delivery of a therapeutic agent (e.g., by a micro-electronic machine or micro-machine).

It will be appreciated that with multi-biomarker detection and subsequent molecular signature production, the present invention can also be used to image and interrogate cellular dynamics during other complex cellular processes, such as embryonic development, cellular growth and differentiation, and cellular changes that occur early in the course of disease. For example, the method can be used to detect different stem cell biomarkers and thereby produce a molecular signature indicative of a particular developmental stage of a stem cell (or other progenitor cell). Additionally, the method can be used to detect different cell biomarkers associated with an inflammatory response and thereby produce a molecular signature indicative of a particular inflammatory response and/or inflammatory disease.

In another aspect, the present application provides a method for treating a disease in a subject. One step of the method can include contacting the cell with a diagnostically effective amount of an imaging composition. As discussed above, the particular components of the first and second imaging probes comprising the imaging composition can be varied depending upon the particular target cell and/or population of target cells to be imaged. The cell can then be contacted with the imaging composition either ex vivo or in vivo (as discussed above). Upon contacting the imaging composition with the cell, one or more imaging modalities can be used to detect a signal that will be generated if the first and second biomarkers are present and in sufficient geometric proximity to one another to allow the first reporter moiety to interact with or complex with the reporter moiety. If one or both of the first and second biomarker is not present, however, and/or the first and second biomarkers are not in sufficient proximity to one another, then the first reporter moiety will not interact with or complex with the second reporter moiety and, thus, a detectable signal will not be generated.

As discussed above, the signal(s) detected by the imaging modality (or modalities) can then be used to produce a molecular signature of the cell. Based on the molecular signature of the cell, the subject can then be appropriately treated for the particular disease by, for example, administering an effective amount of a therapeutic composition. An "effective amount" can refer to that amount of a therapeutic agent that results in amelioration of symptoms or a prolongation of survival in the subject and relieves, to some extent, one or more symptoms of the disease or returns to normal (either partially or completely) one or more physiological or biochemical parameters associated with or causative of the disease. Therapeutic agents can include any agent (e.g., molecule, drug, pharmaceutical composition, etc.) capable of preventing, inhibiting, or arresting the symptoms and/or progression of a disease.

In one example of the present invention, a molecular signal of a cell can indicate that a subject has a particular cancer. Because the type, severity, and stage of the cancer can be determined based on the molecular signature of the cell, the subject can then be administered an effective amount of a chemotherapy agent to treat the cancer. Chemotherapy agents are well known in the art and can include, for example, alkylating agents (e.g., cyclophosphamide, ifosfamide), antibiotics that affect nucleic acids (e.g., doxorubicin, bleomycin), platinum compounds (e.g., cisplatin), mitotic inhibitors (e.g., vincristine), antimetabolites (e.g., 5-fluorouracil), camptothecin derivatives (e.g., topotecan), biological response modifiers (e.g., interferon), and hormone therapies (e.g., tamoxifen).

Alternatively, the imaging composition can be used in a method to identify cells that are treatable by a particular therapeutic agent or therapeutic intervention. Additionally, the imaging compositions and methods can be used to the progress of therapy by monitoring a decreasing signal over time.

A further aspect of the application relates to a method for treating a disease in a subject by contacting a cell associated with the disease with a therapeutic composition. The therapeutic composition can include a first therapeutic probe and a second therapeutic probe. The cell can have a first biomarker and a second biomarker that is different from the first biomarker. The first therapeutic probe can include a first targeting moiety that is linked to a therapeutic agent via a linker region. The first targeting moiety can specifically complex with the first biomarker. The second therapeutic probe can include a second targeting moiety that is linked to a release agent via a linker region. The second targeting moiety is different than the first targeting moiety and specifically complexes with the second biomarker. The release agent of the second therapeutic probe can release the therapeutic agent from the first therapeutic probe when the first therapeutic probe and the second therapeutic probe complex respectively to the first biomarker and the second biomarker of the cell.

The following examples are for the purpose of illustration only and are not intended to limit the scope of the claims, which are appended hereto.

EXAMPLE 1

Example 1 illustrates synthesis of ß galactosidase activated magnetic resonance contrast agents targeted to cell surface receptors.

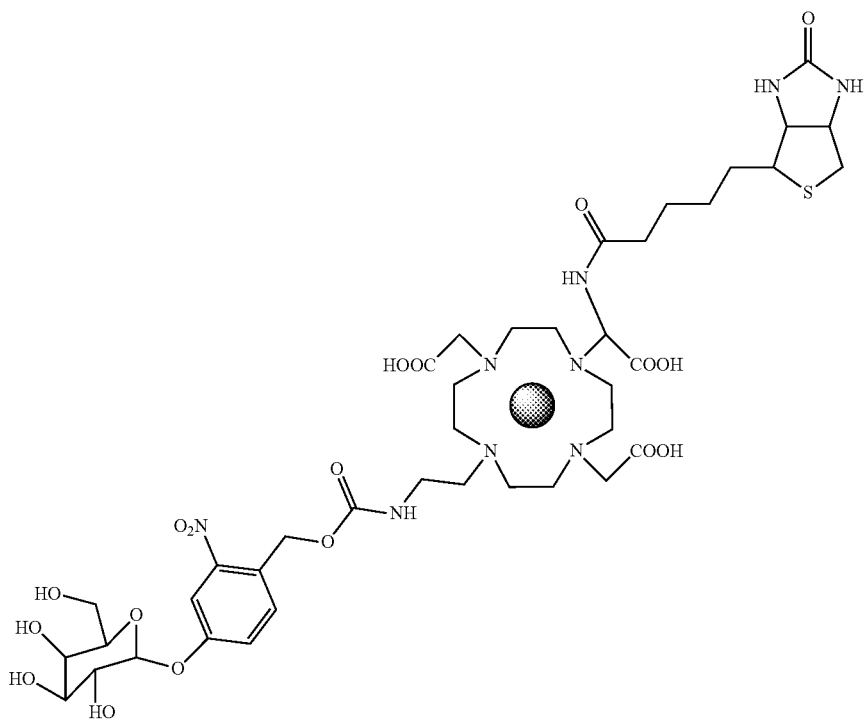

1

-continued
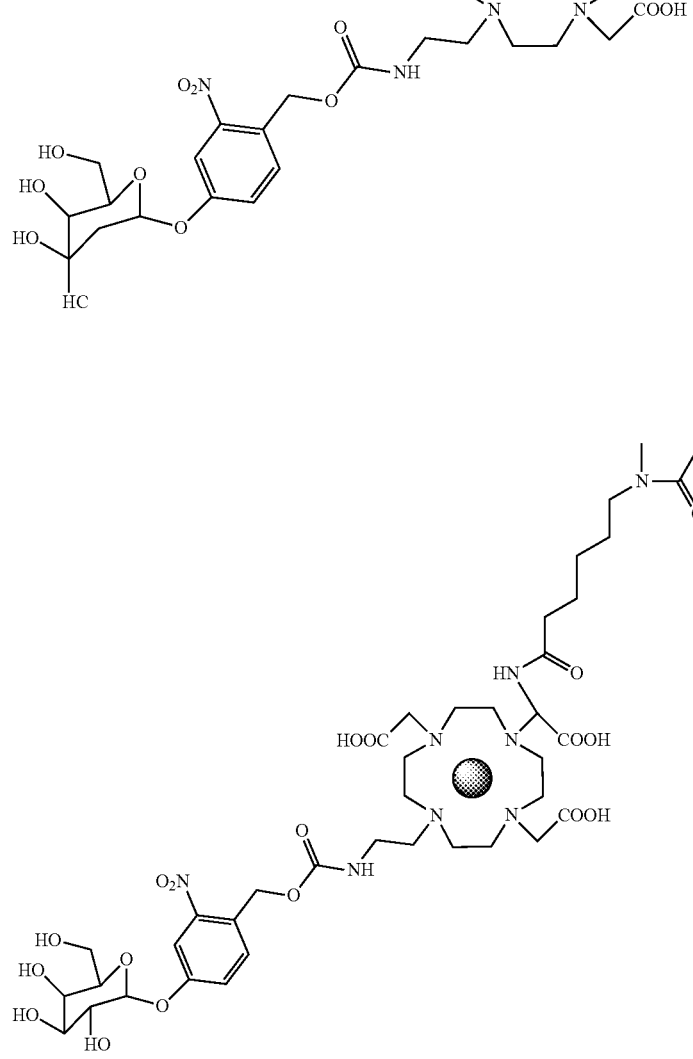
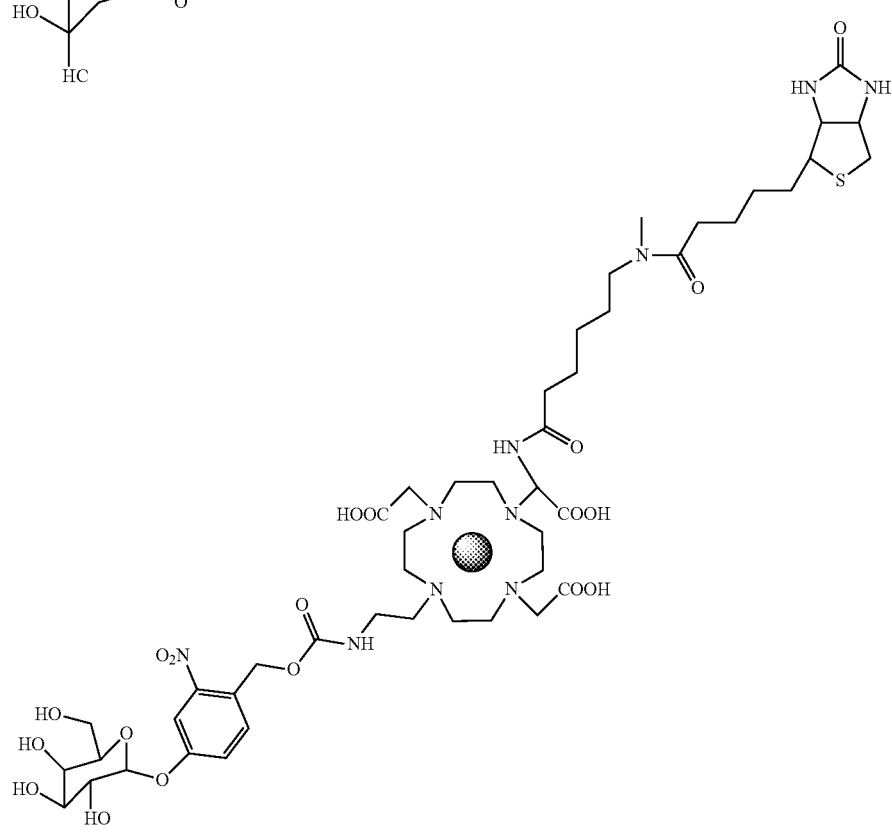

-continued
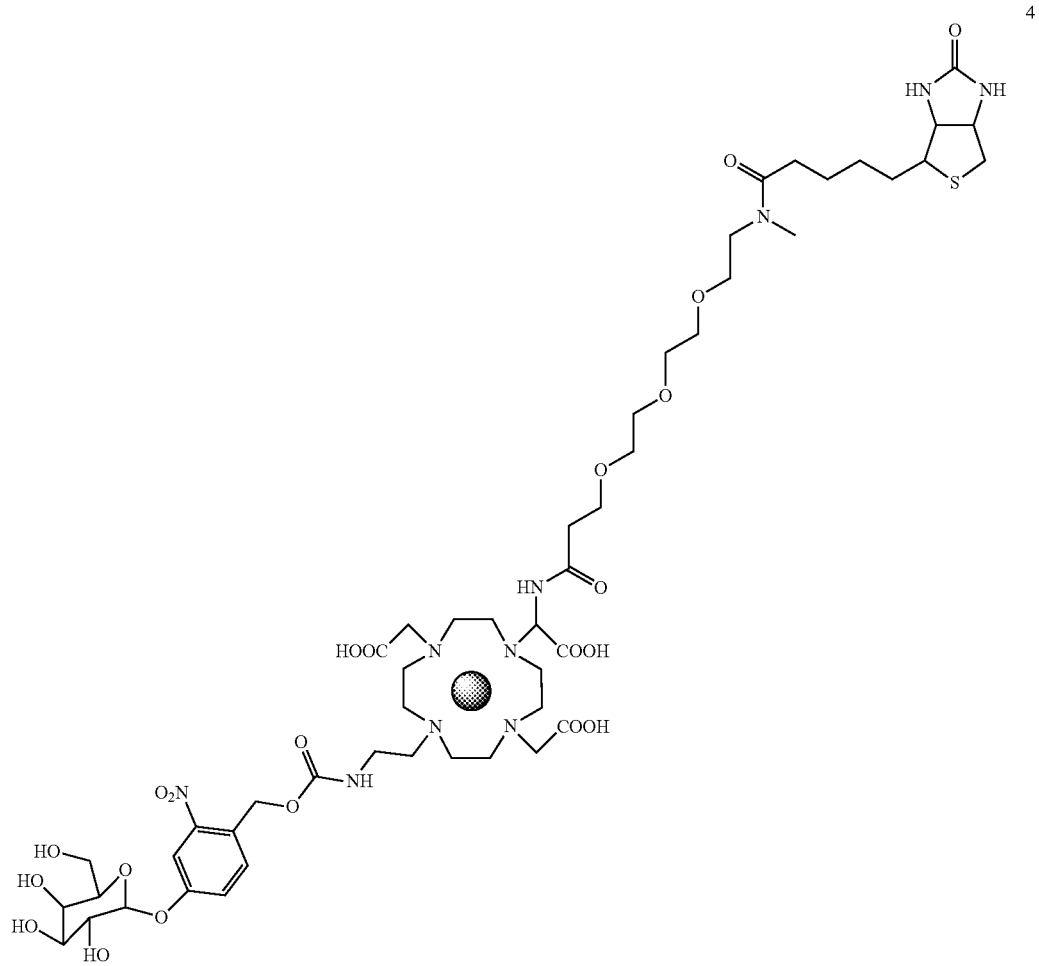
4
Molecules 1 and 2 are derived from general structure I, while molecules 3 and 4 are derived from general structure II. All molecules except 2 (to standardized reaction conditions) are designed to be stable to hydrolyzing action of biotinidase.

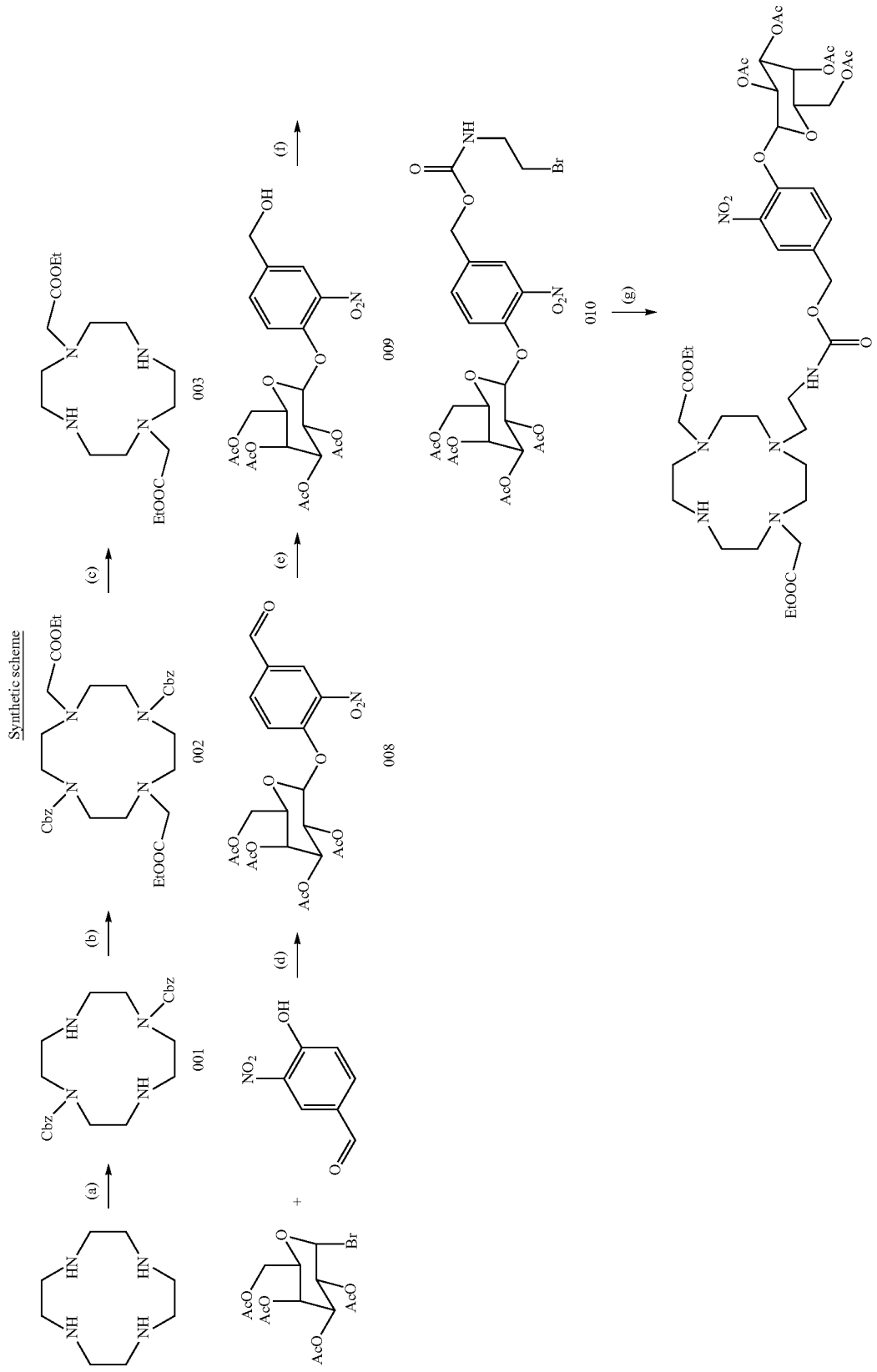
Synthetic scheme
Reaction procedure: Reagent/solvent; yield (a) CbzCl/CHCl₃; 98% (b) BrCH₂COOEt/K₂CO₃; 80% (c) Pd—C/H₂/EtOH; 95% (d) Ag₂O/CH₃CN; 94% (e) NaBH₄/CHCl₃/i-PrOH; 85% (f) Bromoethylisocyanate/DMF; 80% (g) Cs₂CO₃/DMF.

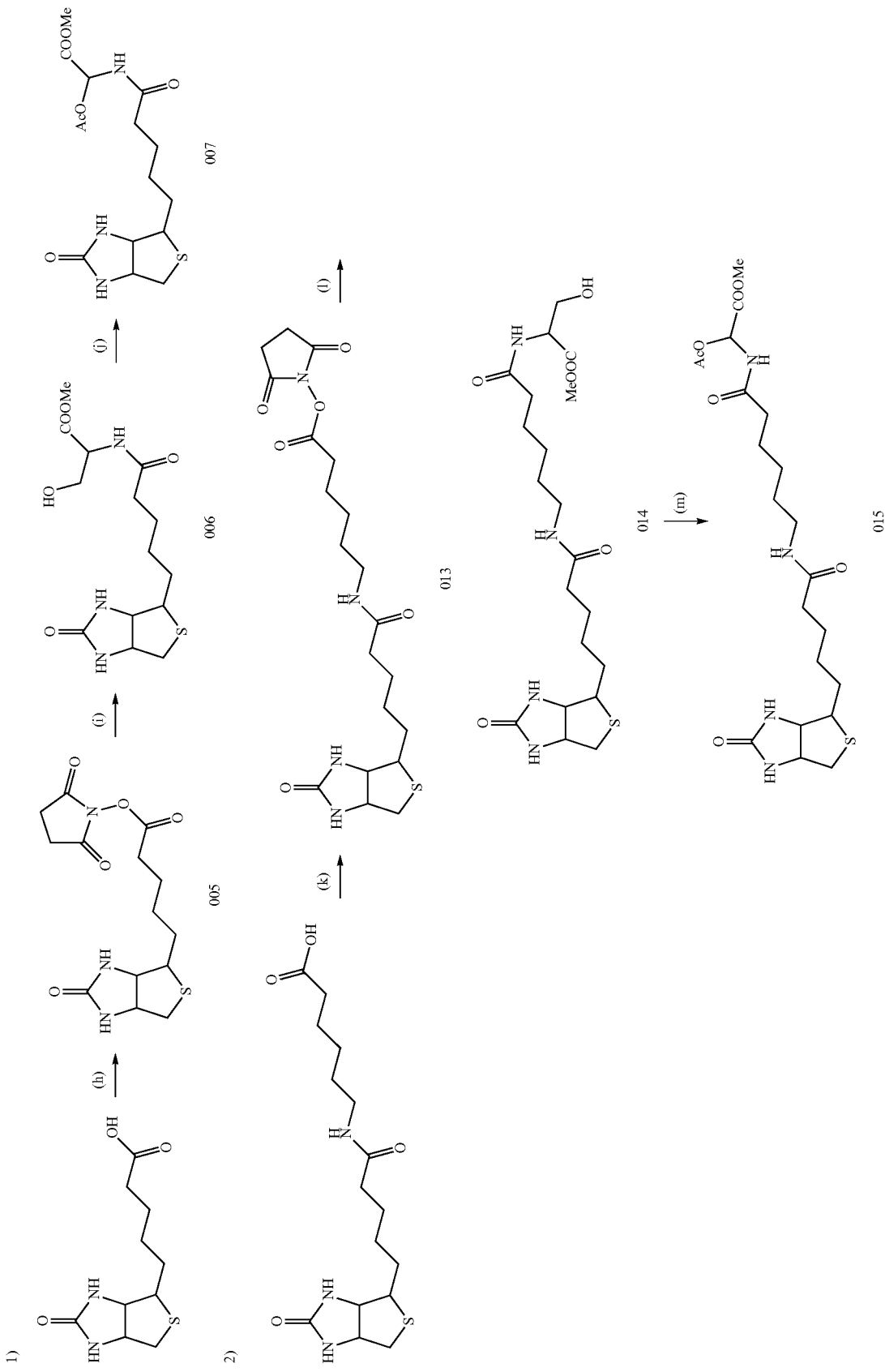

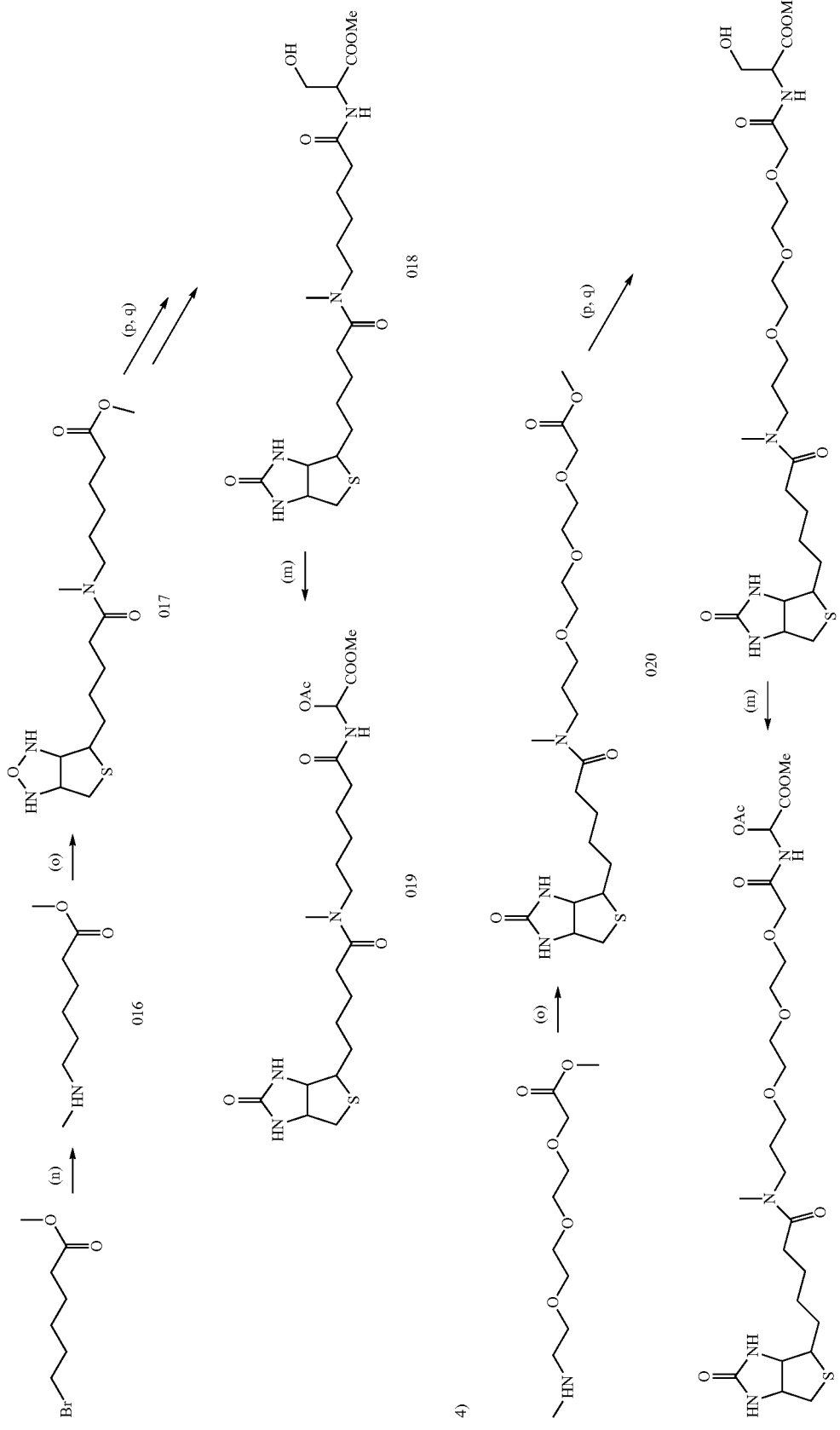

-continued
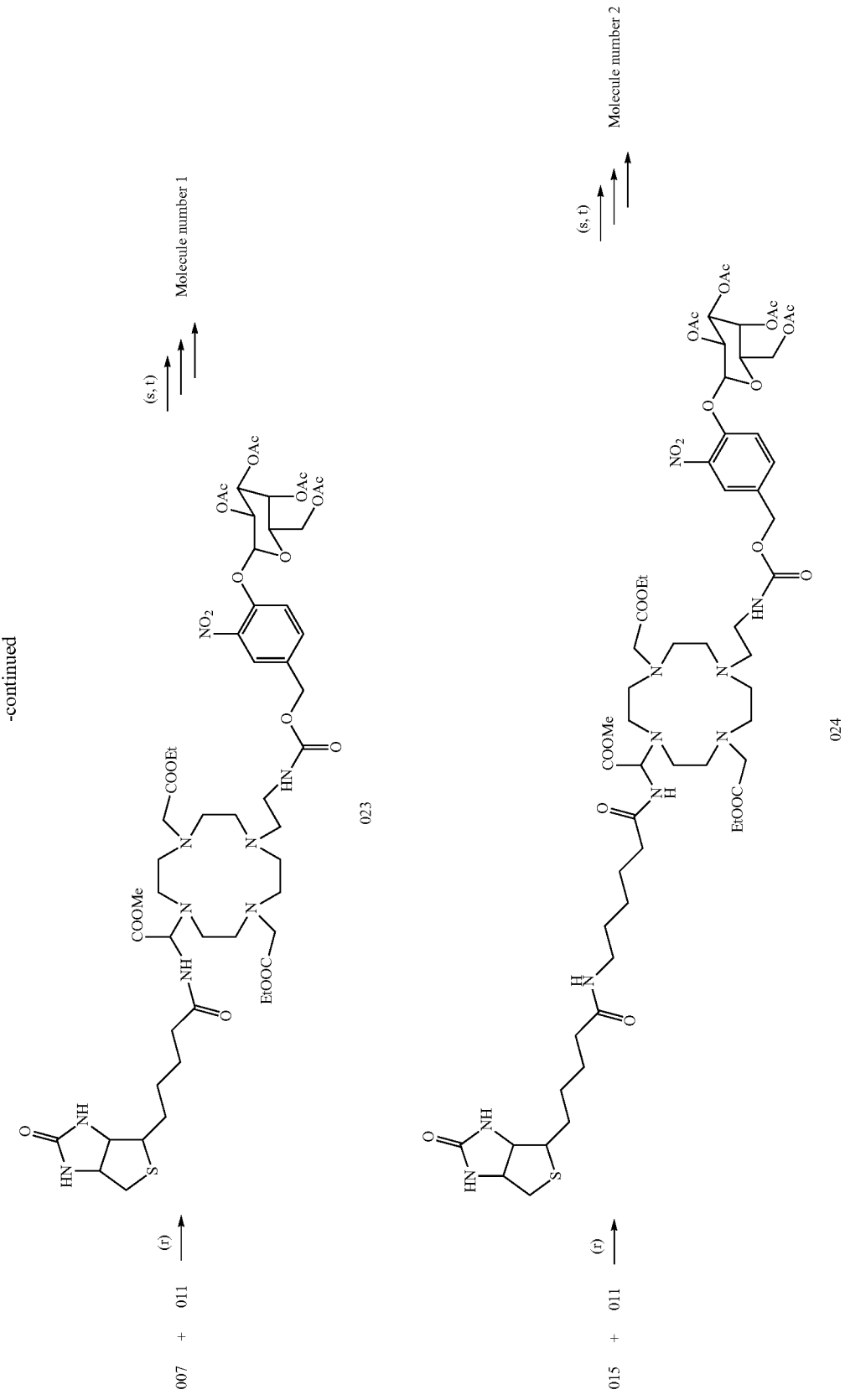

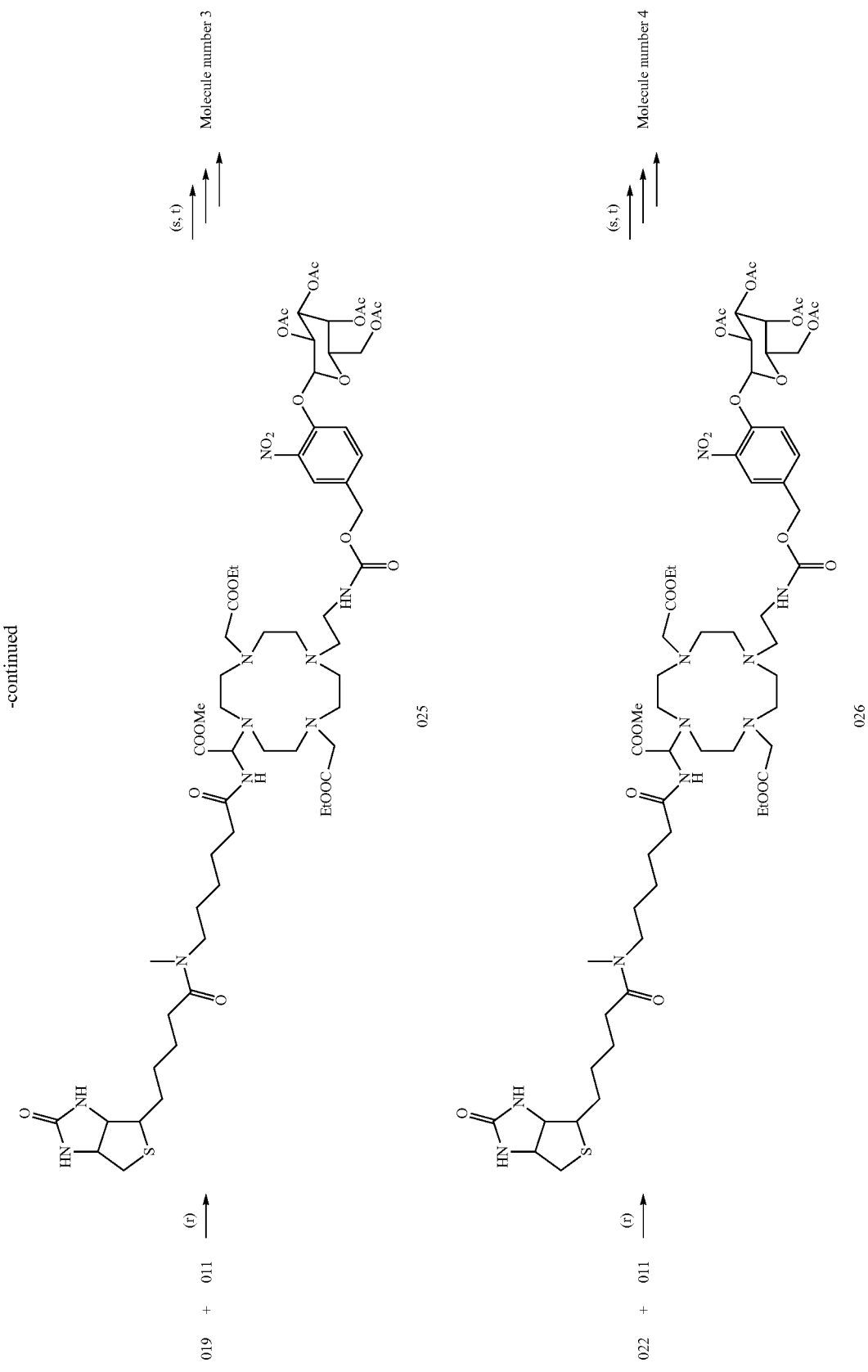

EXAMPLE 2

Targeted-reporter imaging agent platforms answer a critical unmet need and have real application for imaging the multi-step progression of cancer growth. The development of these platforms to investigate molecular signatures associated with disease creates the next frontier in in vivo imaging. Mutational events that drive a normal cell to become a cancer cell require the coordinated overexpression of multiple biomarkers, e.g., cell surface receptors (FIG. 4A). These expression patterns of multiple biomarkers can thus be indicative of the type, stage, or severity of the disease. This is an especially intriguing development since most disease-associated assays depend on single biomarker identification. Given that disease is recognized both by its complexity and progression, single biomarker utilities are self-delimiting. By developing multi-marker imaging, we provide an imaging tool to exploit the accruing molecular understanding of cancers allowing eventual imaging of combinatorial biomarkers that will uniquely identify cancers and predict prognosis noninvasively.

To develop imaging tools that will take advantage of the diagnostic molecular signature, new technologies must employ a contrast agent or signal-amplifying material conjugated to a molecular targeting agent. By linking a reporter enzyme to a targeting moiety signal-amplification at the molecular level can be achieved. To expand this approach, we have engineered enzyme fragments that in themselves have no activity, but will complement in trans to provide robust activation at the cell surface FIG. 4B. Therefore, investigators are only constrained by the number of fragments with which the reporter enzyme can be broken. Thus, by expanding the number of biomarkers available to diagnostic and therapeutic purview, we envision a novel and innovative platform-based approach to disease identification, staging, and treatment FIG. 4C.

Historically, molecular biology reporter assays were developed to monitor gene expression by integrating reporters that were either intrinsically fluorescent or enzymatic. Enzymes, such as β-galactosidase, firefly luciferase, β-lactamase, and alkaline phosphatase, are particularly effective reporters because they are specific, sensitive, and stable in diverse applications. In addition, most enzyme reporters have little to no endogenous expression in mammalian cells, effectively reducing background complications. Enzyme reporters when compared to their fluorescent counterparts are also favored because they can be amplified by prolonged incubation with substrate, thereby increasing reporter sensitivity.

One of the most popular and widely used reporter enzymes is *Escherichia coli* β-galactosidase (β-gal) encoded by the lacZ gene. β-gal can hydrolyze disaccharides such as β-galactosides, including lactose, into monosaccharides. The protein product is extremely stable and resistant to proteolytic degradation. Many substrate detection reagents to measure β-gal's catalytic activity are commercially available for use in calorimetric, fluorescent, and chemiluminescent assays.

β-gal was one of the first enzymes to be broken into spontaneously re-combinable fragments. First sequenced in 1970, β-gal is a homotetrameric protein comprised of four polypeptide chains, each 1023 amino acids long 14. β-gal monomers are further subdivided into five domains with much of the active site formed at the carboxy terminal end of domain 3. β-gal, like most other enzymes, is constitutively active as long as it is properly folded. The ability to restore full enzymatic activity from cleaved fragments is the fundamental basis of α-complementation, a staple of blue/white clonal screening. Based on subtractive deletion mutants, β-gal was originally split into a small amino terminal fragment (residues 3-41, alpha-donor) and the large remaining subunit (alpha-acceptor). The two fragments are inactive separately. But when an alpha-donor subunit links two alpha-acceptor dimers together, intracistronic complementation (dimer-dimer interaction) occurs and restores the active quaternary conformation of β-gal.

In this example, we have engineered completely unique β-gal fragments from those previously identified by truncation mutants. This example shows that the β-gal can be completely re-natured from its unfolded, fragmented monomers as determined by recovery of its enzymatic activity. Individually, the monomer fragments are small, stable, and enzymatically inactive. When the correct combination of β-gal fragments are incorporated in bacteria or correctly oriented in mammalian cells, trans-complementation occurs and full enzymatic activity is restored. Further, we demonstrate the utility of these fragments for targeted-complementation in live cell assays and demonstrate the robustness of the system with an eye on utilizing these fragments to investigate molecular signatures associated with disease.

Experimental Section

Plasmids and Bacterial Strains pSV-β-gal was kindly provided by Dr. Antonio Choicca. pHAT10 vector was purchased from Clontech (Mountain View, CA); pAN4 vector was purchased from Avidity, Inc. (Aurora, CO). *E. coli* K12 ER1793 bacteria were purchased from New England BioLabs (Ipswich, MA). Rat glioma C6 cells were maintained in Dulbecco's modified Eagle's medium (DMEM) supplemented with 10% heat inactivated fetal calf serum (FCS).

β-galactosidase (β-gal) Constructs Creation

Full-length β-gal from the pSV-β-gal plasmid (Promega; Madison, WI) was used as the starting genetic template. DNA encoding the split-β-gal fragment(s) is amplified by PCR using full length β-gal template and primers that introduce flanking restriction enzyme sequences. The PCR product was ligated into a pHAT10 vector (Clontech; Mountain View, CA) containing a suitable antibiotic selectable marker for bacterial propagation. The resulting coding sequence, consisting of the His-tag and split-β-gal fragment, was excised from the vector and inserted into the pAN4 vector (Avidity; Aurora, CO). The pAN4 vector was used to express a single N-terminal biotin-protein fusion.

Propagation of β-gal Extracts

Luria-Bertani (LB) broth (5 mL) containing ampicillin (50 μg/μl) was inoculated with a bacterial scrape (about 25 μL) containing one of the discrete β-gal plasmids and allowed to grow overnight (18-20 hr.) in an incubator/orbital shaker at 37° C. Following the growth period, LB broth (1 L) with ampicillin (50 μg/μl) was inoculated with the 5 mL overnight growth and placed in the incubator/orbital shaker at 37° C. until an absorbance of 0.4 was observed at 600 nm (5.5 hr.). The bacterial culture was then induced with 1 mM IPTG. For subunits α-4, 1-ω, and ω, as well as full length β-gal, the IPTG-induced culture was grown in an incubator/orbital shaker at 37° C. until a reading between 0.8 and 1.0 was observed at absorbance 600 nm (6 hr.). For subunits α-1 and 1-4, the IPTG-induced bacterial culture was grown on a rocker at room temperature for 19 hr. Upon completion, the cells were pelleted and the supernatant discarded. The cell pellet was lysed with lysozyme at room temperature for 20 min. and then stored at −80° C. until purification.

Purification of β-gal Extracts

β-gal subunits were purified from contaminating bacterial cell degradation products and other particles using affinity chromatography. The whole cell lysate was thawed at 37° C., sonicated, and centrifuged. The lysate was passed over a nickel Talon affinity column (Clontech; Mountain View, CA) using gravity flow. The column was washed twice with extraction buffer [50 mM NaHPO$_4$, pH 7; 300 mM NaCl in ddH$_2$O]. The His-tagged protein was eluted off the column in 0.5 mL fractions with elution buffer [0.15 M imidazole in extraction buffer]. Each fraction was analyzed for the presence and concentration of purified protein using standard protein analysis (Bio Rad DC Protein Assay kit; Bio Rad; Hercules, CA) and immunoblot analysis with anti-His (Upstate, Billerica, MA) and HRP-conjugated streptavidin (Chemicon; Temecula, CA). Fractions containing the desired protein were combined, dialyzed against PBS, and stored at 4° C.

β-gal activity assay

For the solution-based activity assay, β-gal fragments were added, either individually or in complementing pairs, to uncoated 96-well microtiter assay plates in equal molar amounts and incubated at room temperature on an orbital rocker for 1 hr. Full-length β-gal (1 mg/ml) was serially diluted to create a standardized concentration curve. At time zero, the assay was initiated by using a 12-channel pipettor to add 20 µl of ONPG (4 mg/ml) to each well of the microplate. In the endpoint assay, the microplates were incubated at room temperature for the appropriate length of time, e.g., 30 min, before the reaction was terminated by the addition of 50 µl of 1 M Na2CO3. Then, the absorbance (420 nm) was read in a Tecan Infinite 200 plate reader (Tecan; San Jose, CA). The absorbance data was transferred to a Microsoft Excel spreadsheet and the amount of ONPG substrate hydrolyzed was calculated.

Western Blot Analysis

Samples were lysed in 200 µL cell lysis buffer (Cell Signaling Technology, Inc.; Danvers, MA) on ice for 10 min., sonicated, and centrifuged at 4° C., 3 min., 13,200 rpm. Protein concentrations were determined by modified Bradford assays performed on supernatants using the DC Bio-Rad Protein Assay Dye kit (Bio-Rad; Hercules, CA). Absorbance was measured at 750 nm using the Tecan Infinite 200 (Tecan; San Jose, CA). Equal protein samples (100 µg) were boiled for 5 minutes in 1× final concentration reducing sample buffer. The samples were run in 10% bis-acrylamide SDS-PAGE running gels for 60 min. at 150V using the mini-Protean 3 electrophoresis system (Bio-Rad; Hercules, CA), then transferred to nitrocellulose membrane using a mini-Protean Transblotter system (Bio-Rad; Hercules, CA) for 60 minutes at 200V. For immunoblotting, the membranes were blocked with 5% condensed milk solution in Tris Buffered Saline-Tween 20 (TBST, 1h, RT). Blots were then incubated with HRP-conjugated HRP in TBST for 1 hr. at room temperature. After three TBST washes (5 min. each), the blots were incubated with ECL chemiluminescence reagent (Immobilon Western Kit; Millipore; Billerica, MA) for 1 min. and exposed to KODAK BioMax Light Film (Kodak; Rochester, NY).

Histochemical Assay for β-gal Activity

The assay was performed according to a protocol described previously (Rossi, F. et al., *Proc. Natl. Acad. Sci. U.S.A.* 94(16):8405-8410, 1997; Mohler, W. A. et al., *Proc. Natl. Acad. Sci. U.S.A.* 93(22):12423-12427, 1996). After transfection with the β-gal constructs for 48 h in a 12-well plate, cells were fixed in 4% paraformaldehyde in phosphate buffered saline (PBS) at 25° C. for 5 min. and rinsed twice with PBS for 5 min. X-gal (5-bromo-4-chloro-3-indolyl-b-D-galactopyranoside; Sigma; St Louis, MO, USA) was diluted to a final concentration of 1 mg/mL in 5 mM K$_3$Fe(CN)$_6$, 5 mM K$_4$Fe(CN)$_6$, 2 mM MgC12 in PBS, applied to cells, and incubated at 37° C. overnight. Cells were rinsed twice with PBS for 5 min. Images were captured by a Retiga EXi camera connected to a Leica DM4000 B upright microscope (Leica Microsystems; Wetzlar, Germany).

Targeted-Reporter Complex Assay for Live Cells

Biotinylated ligands for the epidermal growth factor receptor (EGFR) or transferrin receptor (TfR) (B-EGF and B-Tf, Invitrogen; Carlsbad, CA) were linked to biotinylated split-β-gal fragments using streptavidin. Ligand, linker, and reporter fragment were mixed in a molar ratio 1:1:3 at room temperature for 1 hr. Excess D-biotin was added to block any remaining unbound streptavidin sites. The ligand-complex was then diluted to 500 µl with cell feeding media (DMEM, 10% fetal bovine serum, 1% penicillin-streptomycin) and added directly to coverslips seeded with cells overexpressing both human EGFR and TfR. Cells were preincubated with EGF ligand-complex for 15 min and rinsed prior to the addition of Tf ligand-complex for an additional 10 min at 37° C. The cells were then fixed with 4% paraformaldehyde, rinsed with X-gal wash buffer, and stained overnight at 37° C. with 1 mg/ml X-gal as described previously. Images were captured by a Retiga EXi camera connected to a Leica DM4000 B upright microscope (Leica Microsystems; Wetzlar, Germany).

Results

Enzyme candidates for the split-protein fragment approach are readily accessible in nature. We utilized selection criteria that took into account basic enzyme characteristics such as high substrate specificity, lack of (or low level) endogenous expression in mammalian cells, activity at physiologic pH, defined molecular structure including subdomain functional activities, and low toxicity when the enzyme is subsequently introduced into eukaryotic cells. Of the plethora of enzymes, β-gal was one of a very select few enzymes that fit the criteria. Further, β-gal can be used to monitor targeted-complementation, in vitro, in cultured cells.

Figure 5:
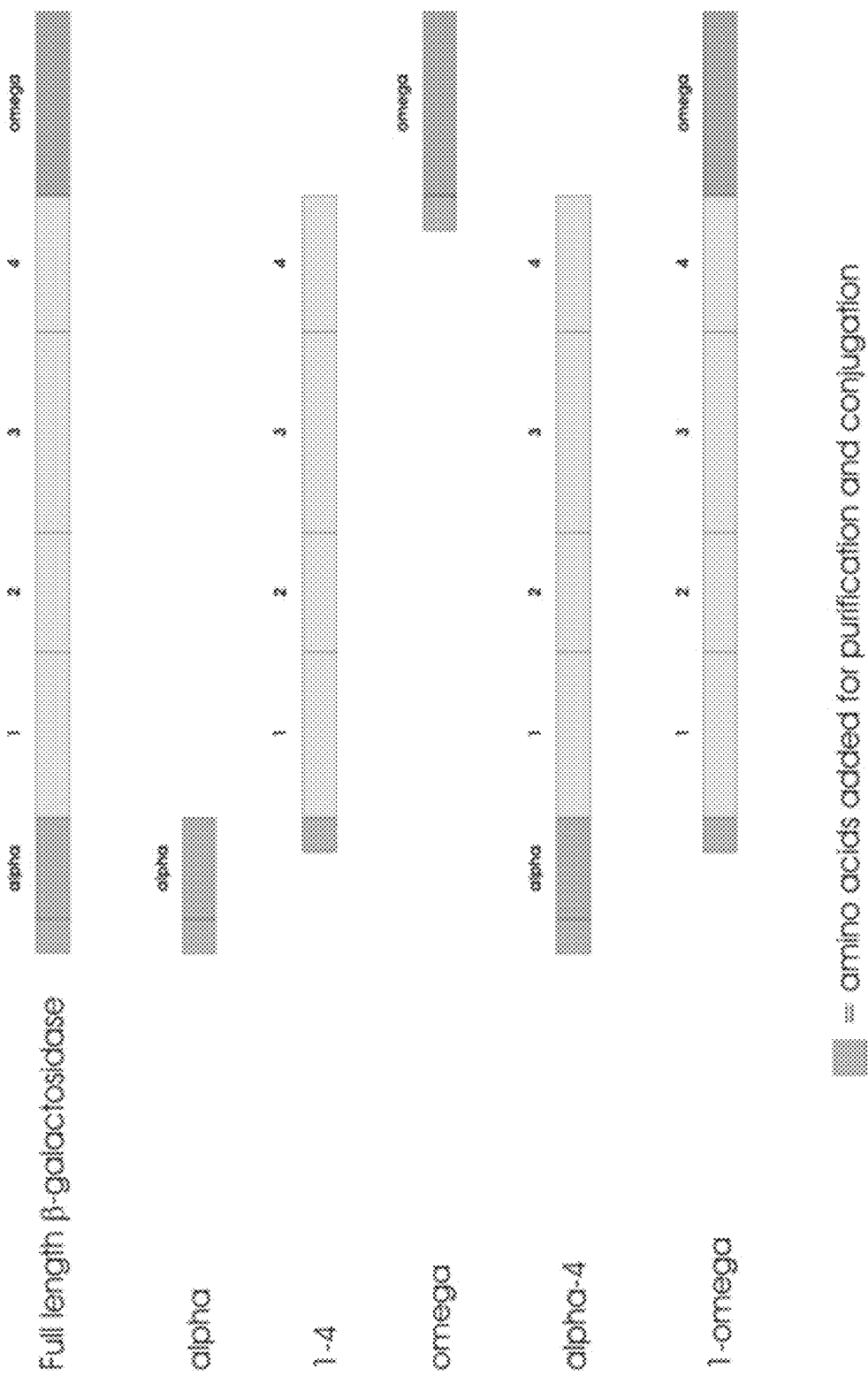
FIG. 5 illustrates β-galactosidase (β-gal) constructs. Full-length β-gal cDNA was cut into varying lengths by restriction enzyme digestion. Each fragment incorporates a necessary domain for β-gal complementation. cDNA fragments were ligated in frame into the bacterial expression plasmid pAN, which adds a biotin to the amino terminus of each β-gal fragment. Each plasmid was expressed in bacteria, IPTG-induced, and purified over a TALON (Clontech Laboratories, Inc., Mountain View, CA) resin column. The expression and purity of the proteins was verified by Western blot analysis. An equal amount of whole cell lysate (100 μg) was electrophoresed and transblotted onto nitrocellulose paper.

To achieve this, β-gal was first split into multiple polypeptides (FIG. 5). The polypeptides were engineered based on the five discrete domains identified by x-ray crystallography (Jacobson, R. H. et al., *J. Mol. Biol.* 223(4):1177-1182, 1992). We used the β-gal gene encoding amino acids 10 through 1023 from the plasmid pSV-β-gal (Promega; Madison, WI) as the starting genetic code. The split-β-gal fragments were designed to create individual bi-complementing pairs: alpha domain and the 1-omega domain, alpha-4 domain and the omega domain. A third domain, 1-4, was also constructed to recreate tri-complementation between the alpha domain and the omega domain.

To yield acceptable levels of β-gal fragments from bacteria, the exact location of the translational start and stop sites for each polypeptide was empirically determined. The resulting biotin-tagged, His-tagged split-β-gal fragments were then propagated, expressed, and purified from *E. coli*. Data demonstrate the success of the initial step and show the purity of several β-gal fragments after single step purification over a cobalt affinity column. The yield for each of the fragments was approximately 1 mg per liter bacteria.

β-gal activity can be detected in vivo in *E. coli* in the presence of X-gal (β-gal substrate) and Isopropyl β-D-1-thiogalactopyranoside (IPTG), a feature that can be used to screen for bacterial colonies that express β-gal. In a systematic screen for trans-complementation-competent β-gal fragments in bacteria that does not express endogenous β-gal, strain ER1793, we found several fragment pairs that complement to recapitulate enzyme activity (FIG. 6A). Different combinations of the constructs were used to transform ER1793 bacteria (a bacterium devoid of any β-gal protein). Only combinations of fragments that contain the full complement of the five β-gal domains, α, 1-4, and ω, yielded activity via trans-complementation. None of the individual fragments restore activity to the β-gal deletion strain ER1793. Also, incomplete combinations of fragments are devoid of β-gal activity (not shown). Western blot analysis of whole bacterial extracts from these clones confirmed the expression of split-β-gal fragment(s) in the bacteria (FIG. 6B). Although the proteins were expressed in the bacteria at similar levels, some complementing pairs, i.e., α-4 and 1-ω and α-4 and ω, were better transactivating partners when compared to α-1 and 1-ω.

To test the ability of the split-fragments to spontaneously refold and aggregate into tetramers in solution, complementing pairs of β-gal fragments were combined and assessed in a solution-based activity assay. Levels of active β-gal expression were measured by its catalytic hydrolysis of ortho-nitrophenyl-β-D-galactopyranoside (ONPG), a synthetic chromogenic substrate, to orthonitrophenol (ONP), a yellow product ($\lambda_{max}$=420 nm). Enzyme activity was measured by the rate of appearance of the yellow color using a spectrophotometer. First, purified full length biotinylated β-gal activity was measured against commercially available, lyophilized β-gal (FIG. 7A). Increasing amounts of enzyme were assayed in the presence of ONPG. Enzyme activity was virtually identical for purified recombinant biotinylated-β-gal prepared in the laboratory versus purchased β-gal.

Figure 7C:
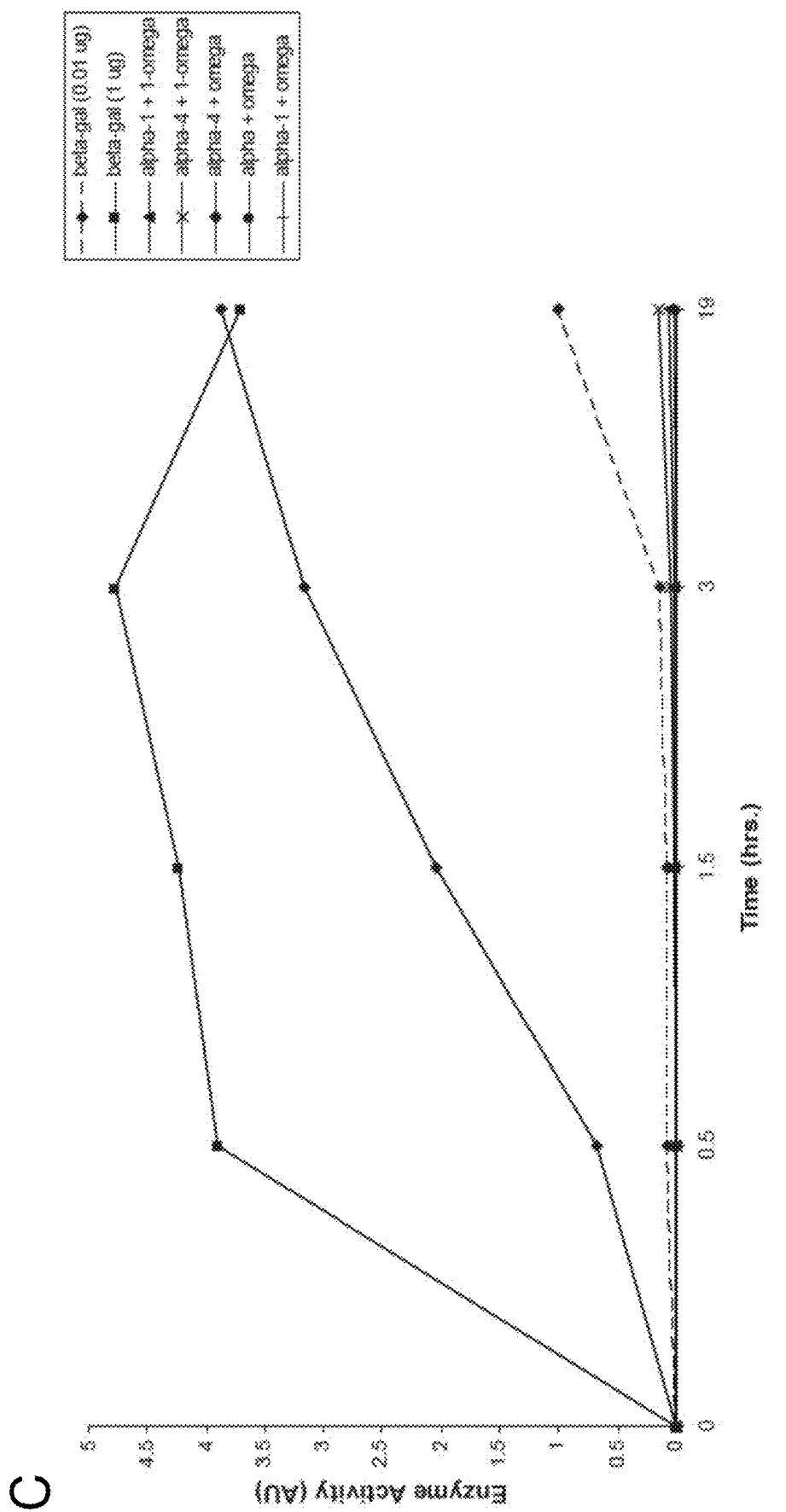

The folding mechanism of β-gal is known to occur in three stages: formation of secondary dimer structures from monomeric primary structure (fast), structural rearrangement of dimers (slow), and association of dimers into tetramers (fast) (Nichtl, A. et al., J. Mol. Biol. 282(5):1083-1091, 1998). Assuming that the slowest tetrameric folding proteins require many minutes or hours to fold under simulated conditions, we combined β-gal fragments in equal molar amounts and allowed them to interact for 1 hr at room temperature (FIG. 7B). We then incubated the combinations with ONPG substrate for 30 min. and measured absorbance at 420 nm. Most complementing pairs of β-gal fragments did not reconstitute full β-gal activity in solution. This is clearly a desired result since we did not want indiscriminate complementation of the β-gal fragments in solution. To check our selected refolding/association time, we assayed β-gal enzymatic activity over a range of time points (FIG. 7C) and calculated the enzyme activity. Full-length β-gal was used as the standard control. Complementing pairs α-1, 1-ω and α-4, 1-ω did not produce any perceivable enzyme activity. Non-complementing pairs that do not reconstruct the full-length β-gal also did not have enzymatic activity. Only the combination of α-4 and ω resulted in the spontaneous reformation of β-gal after a 0.5 hr. association time.

Next we examined whether split-β-gal fragments could recombine when transfected into mammalian cells in vivo. Rat C6 glioma cells were transiently transfected with each of the constructs, either singly or in combination. Only in cells co-transfected with combinations of complementing fragments could any β-gal activity be detected (FIGS. 8A-D). In control transfections, in which C6 cells did not receive a complete complement of all the subunits, no β-gal activity was detectable (not shown).

To demonstrate the utility of our reporter fragments in identifying multiple biomarkers, we created a complex as outlined in FIG. 4B that consisted of a reporter fragment, a linker, and a targeting moiety, in this case a ligand. We designed two experiments to determine whether the individual targeted ligand-complexes retained their ability to bind cell surface receptors and whether the individual β-gal fragment ligand-complexes were able to re-establish full β-gal activity when oriented on the cell surface. First, we created a rat 9 L gliosarcoma cell line stably over-expressing two human cell surface receptors, TfR and EGFR. We assayed the expression level of the human receptors by immunoblot analysis (FIG. 9A). In addition, we demonstrated the localization of the human receptors at the cell membrane and to a lesser extent within the cell's interior (FIG. 9B).

Figure 10C:
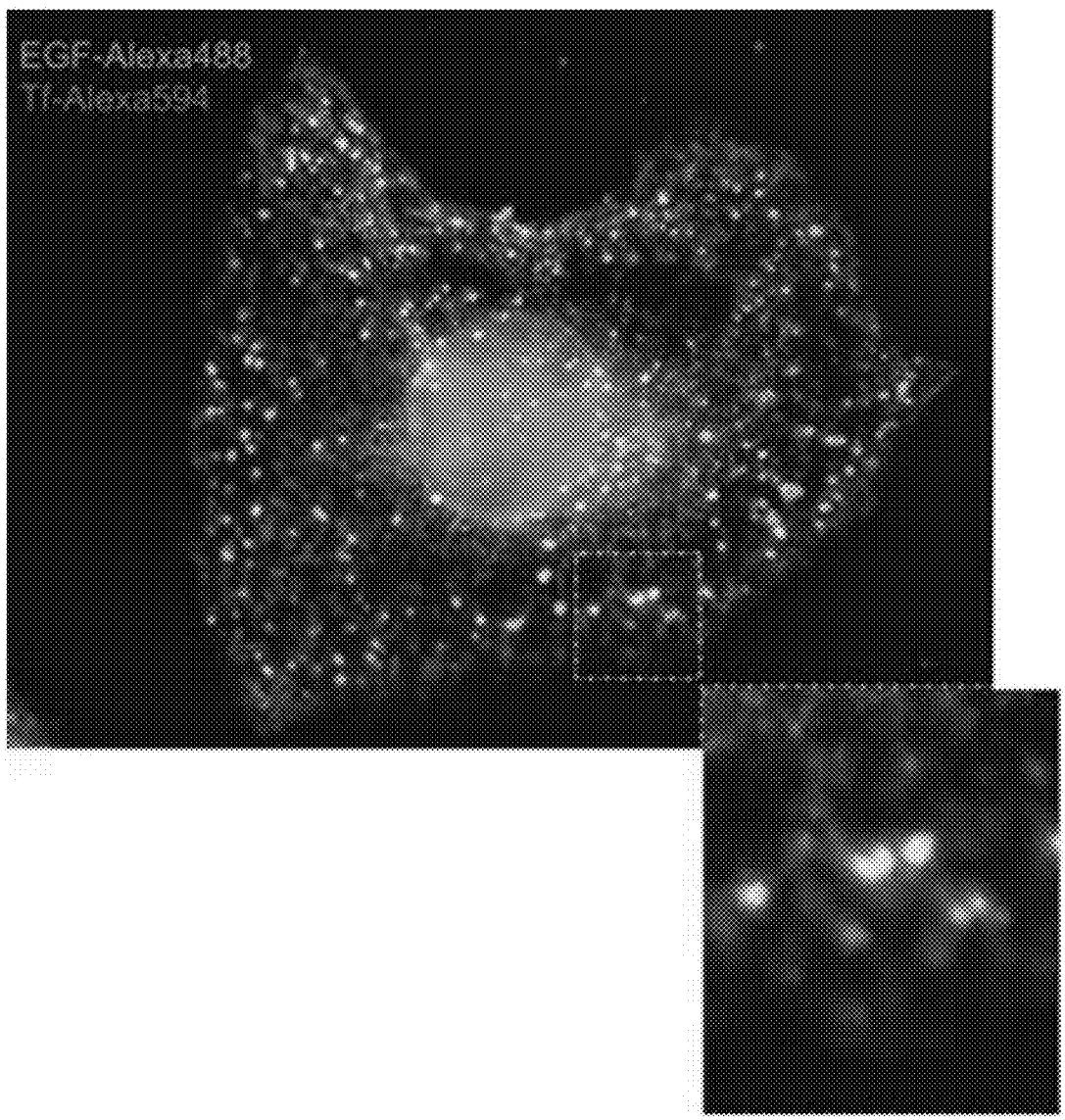

To show that the human receptors were functionally active, cells overexpressing both receptors were stimulated with a cocktail of Alexa488-conjugated EGF and Alexa594-conjugated Tf (Molecular Probes; Eugene, OR) and observed using fluorescence microscopy. Activated EGFR and TfR rapidly internalized their respective ligands into clearly delineated endocytotic vesicles (FIG. 10A). The majority of human EGFR and TfR cycled independently, however, when cells were stimulated simultaneously by their respective ligands. To shift the receptors to the same temporal location within the endocytotic vesicles, we examined receptor co-localization by first pre-loading cells over-expressing both receptors with Alexa488-EGF for 15 min. and then incubating them with Alexa594-Tf at increasing time points (FIG. 10B). Minimal receptor co-localization was detected after a 5 min. exposure to Alexa594-Tf. Increased co-localization was observed after 10 min. FIG. 10C shows a representative cell at high magnification in which a sub-population of vesicles contained both human receptors after a 15 min. pre-incubation with Alexa488-EGF and 10 min. incubation with Alexa594-Tf.

Figure 11:
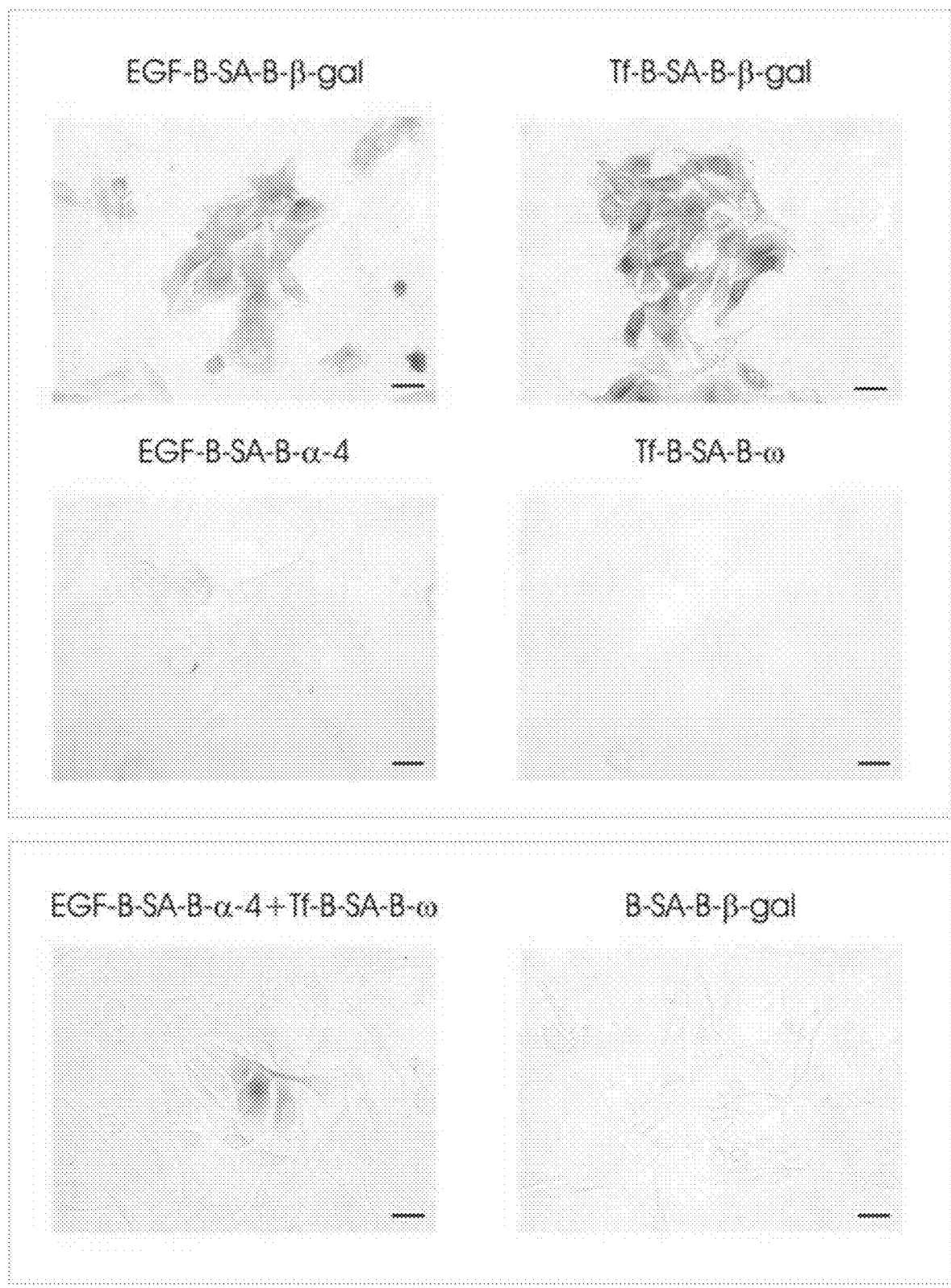
FIG. 11 illustrates receptor-targeted β-gal complementation and cell viability after incubation with ligand-targeted reporter complexes. Cells overexpressing human receptors, EGFR and TfR, were incubated with full length β-gal reporter (0.1 nMole) targeted to either the EGFR or TfR. X-gal staining revealed uptake of the ligand-targeted reporter complex (top panels). In the bottom panel, EGF was linked to the α-4 β-gal fragment and Tf was linked to the ω β-gal fragment. When serially incubated on live cells, enzymatic complementation was observed after X-gal staining (images were taken at 20× magnification; scale bar represents 10 µm)

Next, ligand-complexes were formed with the full-length β-gal enzyme reporter. When the cells were incubated with the EGF ligand complex or the Tf ligand-complex, for 15 min or 10 min, respectively, the ligand-complex was internalized and enzymatic activity was successfully visualized after X-gal staining (FIG. 11 top panel). More than 75% of all the cells overexpressing the two human receptors were labeled with either EGF-B-SA-B-β-gal or Tf-B-SA-B-β-gal. In an attempt to capture the sub-population of receptors cycling together in vesicles illustrated in FIG. 10B, individual ligand-complexes were generated with a β-gal reporter fragment instead of the full length enzyme. Biotinylated-EGF was linked to biotinylated α-4 and biotinylated Tf was linked to biotinylated ω. Live cells expressing both human receptors were serially incubated with first one ligand-complex, washed, and then the other complementing ligand-complex. The cells were extensively washed and fixed with 4% paraformaldehyde. Enzymatic activity was visualized by overnight X-gal staining (FIG. 11 bottom panel). Cells incubated with individual ligand-reporter fragment complexes, EGF-B-SAB-α-4 or Tf-B-SA-B-ω, did not stain positive for enzymatic activity (FIG. 11 top panel). Ligand-reporter fragment complexes did not adversely affect cell viability after incubation or growth rate of cells after complex removal as demonstrated by trypan blue cell staining.

EXAMPLE 3

Heterotic Human Brain Tumors can be Imaged with EGFR-targeted β-gal

Figure 12:
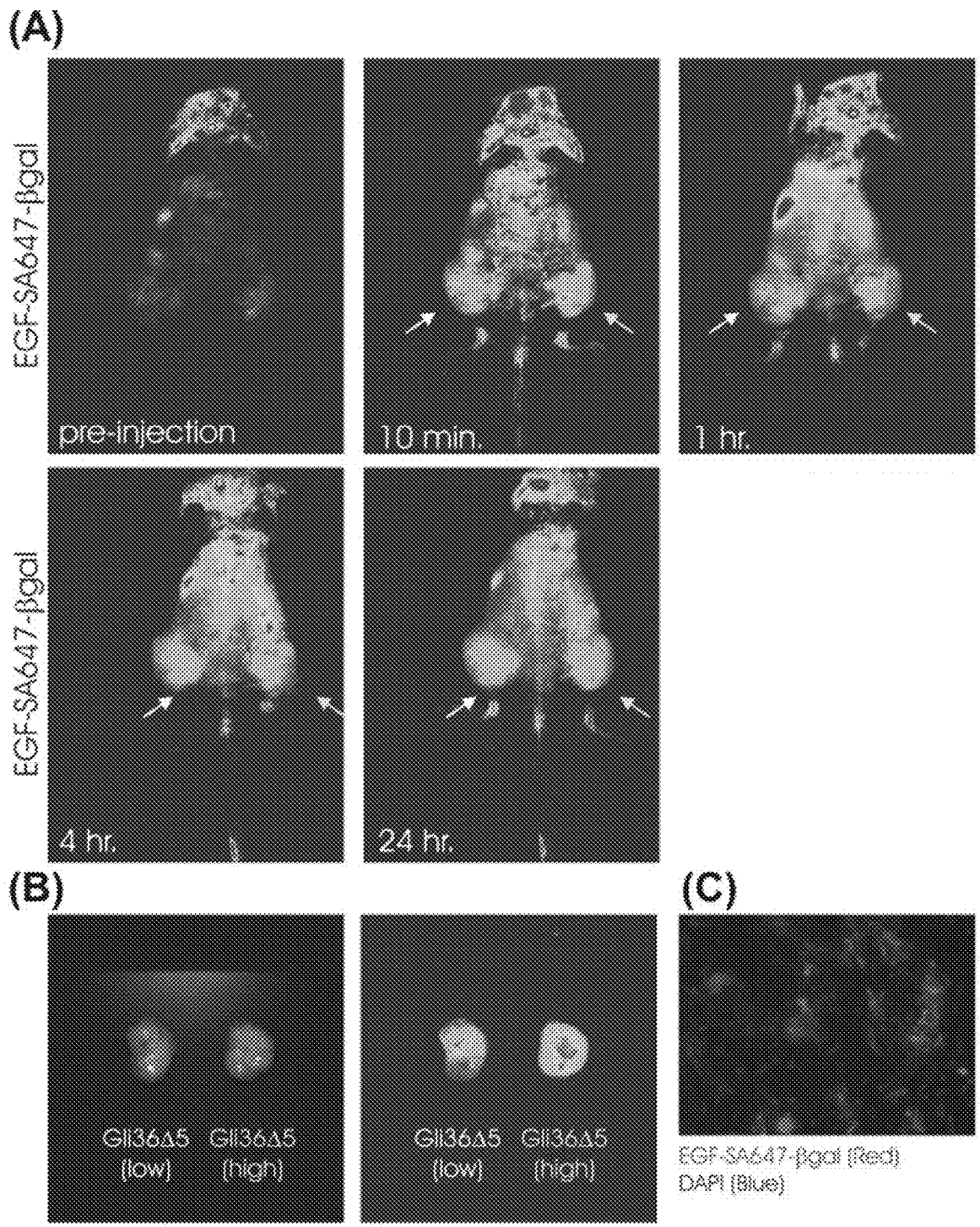
FIGS. 12A-C show the results of in vivo targeting of heterotopic human brain tumors with an EGFR-targeted β-gal reporter complex.
Figure 13:
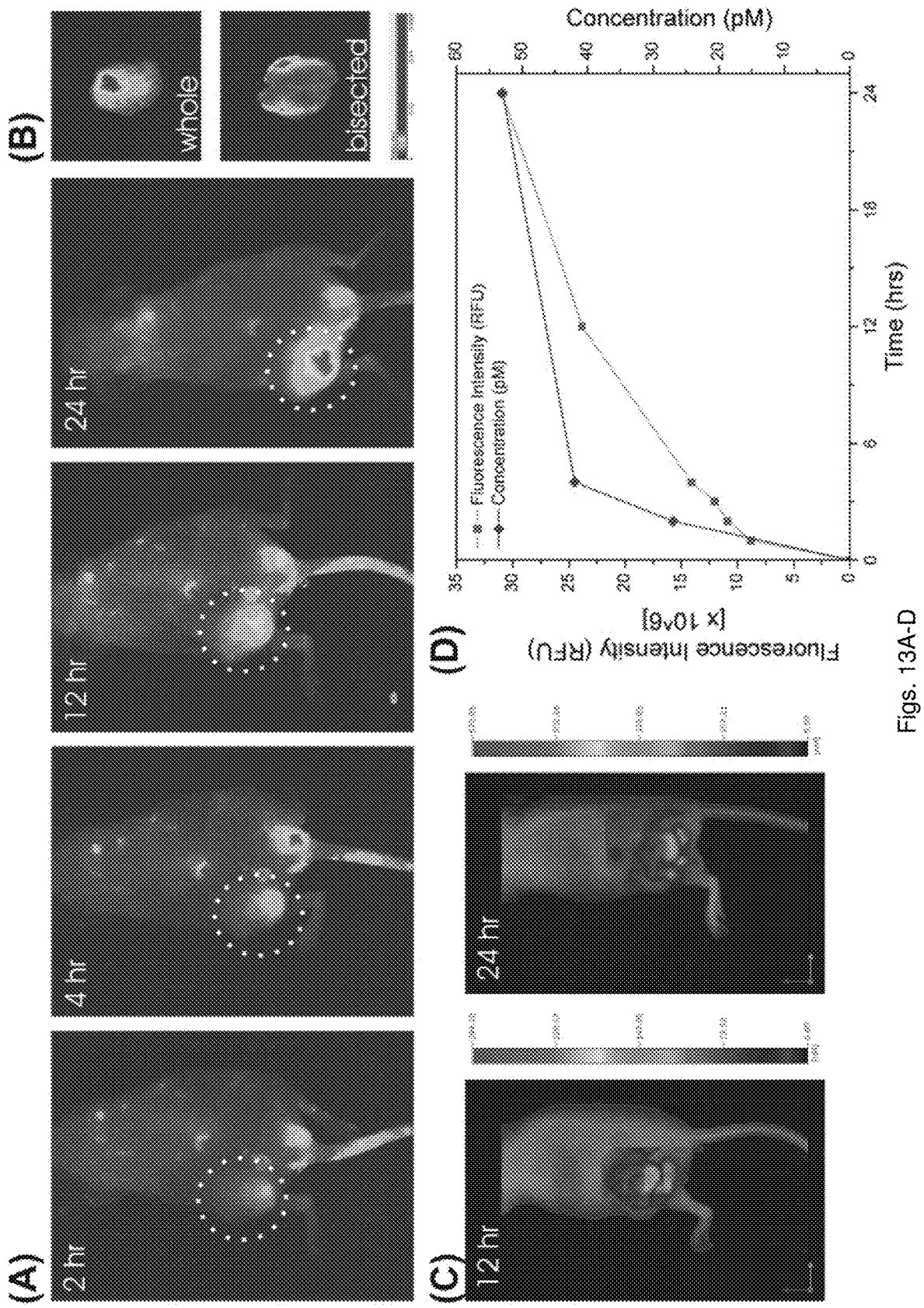
FIGS. 13A-D show the results of in vivo targeting of heterotopic human brain tumors with a TfR-targeted β-gal reporter complex.

Human tumor cell lines, Gli36Δ5, over-expressing EGFR and TfR, were implanted subcutaneously on the flanks of mice and grown for 21 days as per IUCAC approved protocols. Mice were intravenously injected with EGF-B-SA647-B-β-gal and imaged over a 24 hr period. Fluorescence from the Alexa 647-conjugated streptavidin linker is measured using a small animal fluorescence imaging system (Maestro; Woburn, MA) (FIG. 12A). EGF-B-SA647-B-β-gal is delivered and accumulates in the tumors (arrows). Ex vivo fluorescence imaging (FIG. 12B) and epi-fluorescence (FIG. 11C) of excised and cryosectioned, respectively, tumors confirms uptake and cellular localization of EGF-B-SA647-B-β-gal. 3-D quantitative determination of Tf-B-SA647-B-β-gal distribution in heterotopic tumors of live animals Using fluorescence molecular tomography (FMT), we were able to resolve and quantify fluorochrome concentrations (to pM) in whole animals and tissues in conjunction with in vivo fluorescence imaging (FIGS. 13A-C). Mice were implanted subcutaneously with Gli36Δ5 as above, intravenously injected with Tf-B-SA647-B-β-gal (23 mg Tf/kg mouse), and imaged over a 24 hr period. Fluorescence from the Alexa 647-conjugated streptavidin linker was measured in the live mouse using the small animal fluorescence imaging system; signal accumulated within the tumor over time (FIG. 13A). Excised tumors retained fluorescence (FIG. 13B). Next, the mice were imaged using FMT (FIG. 13C). By generating a ROI over each flank tumor, we were able to calculate the concentration of delivered Tf-B-SA647-B-β-gal (6.7 μM injected dose) to the flank tumor after 24 hrs using targeted β-gal complexes as approximately 53 pM (FIG. 13D).

EGFR-targeted β-gal Complex Accumulates in Orthotopic Brain Tumors

Figure 14:
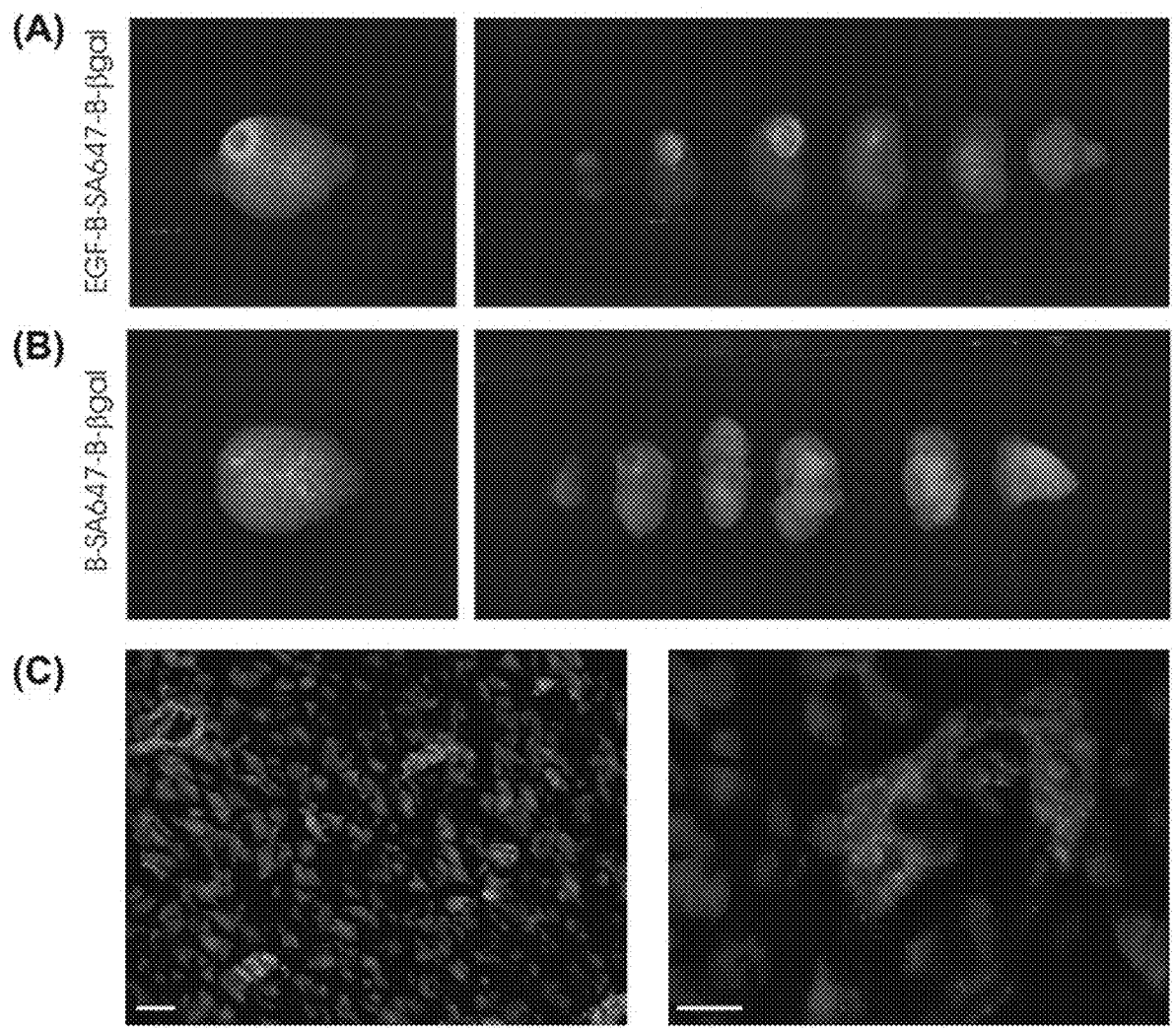
FIGS. 14A-C are a series of images showing ex vivo imaging of orthotopic human brain tumors with a receptor-targeted β-gal reporter complex.

The human glioma cell line, Gli36Δ5, over-expressing human EGFR and TfR, were stereotactically implanted in the brains of mice and grown for 10 days as per IUCAC approved protocols. Mice were intravenously injected with EGF-B-SA647-B-β-gal. After 4 hrs, the mice were euthanized and the brains were removed and imaged whole and then serially transected and imaged again ex vivo using both the Maestro imaging system (FIG. 14A). Both non-targeted and targeted β-gal complexes cross the blood brain barrier. EGF-B-SA647-B-β-gal specifically accumulates in the tumor within 4 hrs (FIG. 14A). In contrast, non-targeted B-SA647-B-β-gal does not accumulate in the tumor as indicated by a lack of fluorescent signal, but remains in the ventral cerebral and cerebellar arteries of the brain (FIG. 14B). Serial sections of the brains were cryosectioned and counterstained with DAPI to delineate cell nuclei (FIG. 14C). Epi-fluorescence images captured at 40× (left) and 100× (right) clearly show significant EGF-B-SA647-B-β-gal uptake within the tumor and internalization within the cells' cytoplasm. Differential identification of EGFR levels in orthotopic brain tumors using EGF-B-SA647-B-β-gal.

Figure 15:
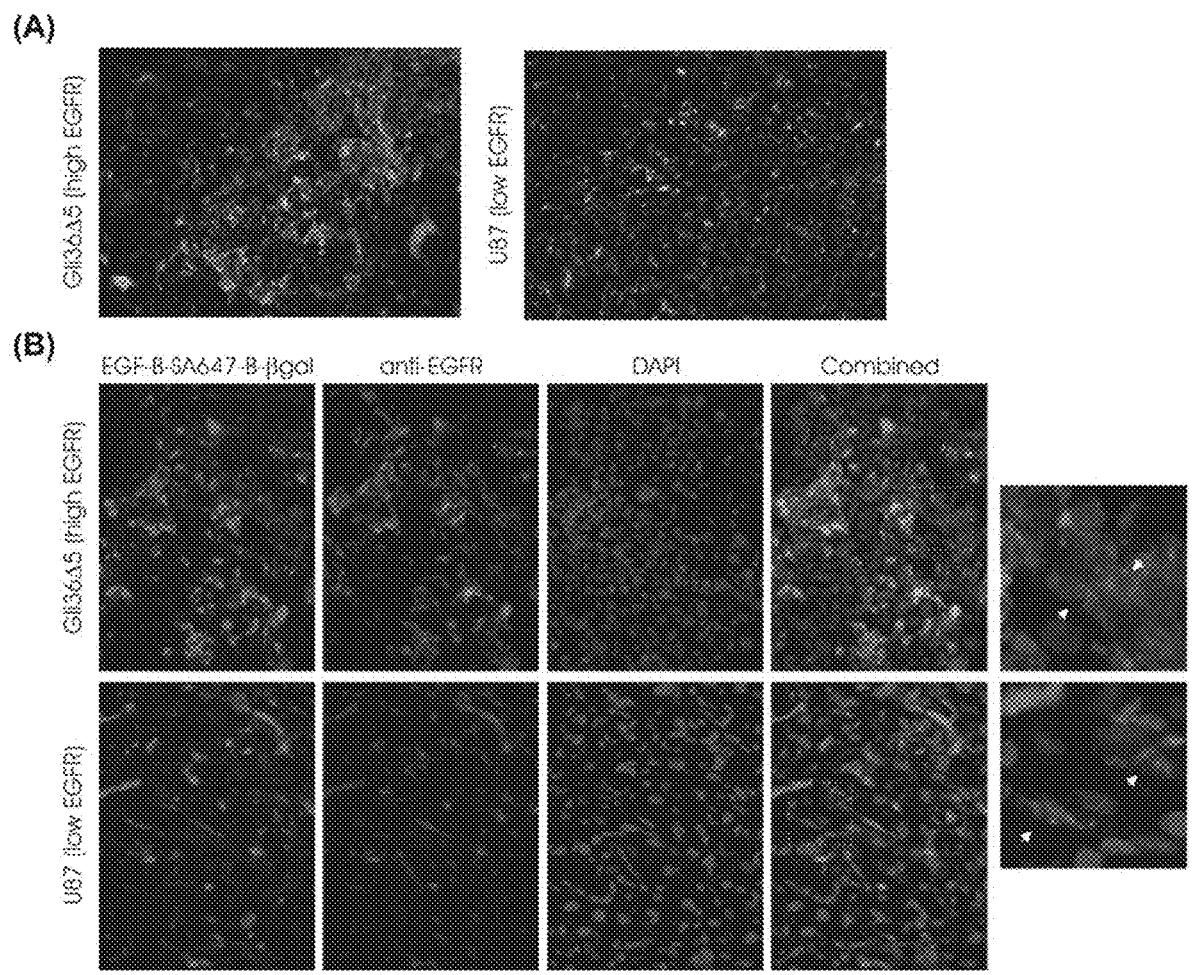
FIGS. 15A-B are a series of images showing varying levels of EGFR in orthotopic human brain tumors visualized ex vivo with an EGFR-targeted β-gal reporter complex.

Mice implanted with orthotopic tumors created from human cell lines either expressing high levels of EGFR (Gli36Δ5) or low levels of EGFR (U87) were intravenously injected with EGF-B-SA647-B-β-gal to demonstrate that we can distinguish between tumors with variable expression levels of EGFR. After 4 hrs, the tumors were excised, cryosectioned, and counterstained with anti-EGFR to reveal receptor presence and co-localization with targeted-β-gal complex (FIGS. 15A-B). Gli36Δ5 tumors expressed high levels of EGFR (FIG. 14A, green), while U87 tumors expressed very low levels of EGFR. In addition, our orthotopic Gli36Δ5 tumors expressed EGFR heterogeneously, similar to expression patterns observed in carcinoma in situ. Microscopic observation (40× magnification) shows that EGF-B-SA647-B-β-gal (red fluorescence) accumulates specifically within the cells expressing EGFR (green fluorescence) (FIG. 15B).

EXAMPLE 4

Figure 16:
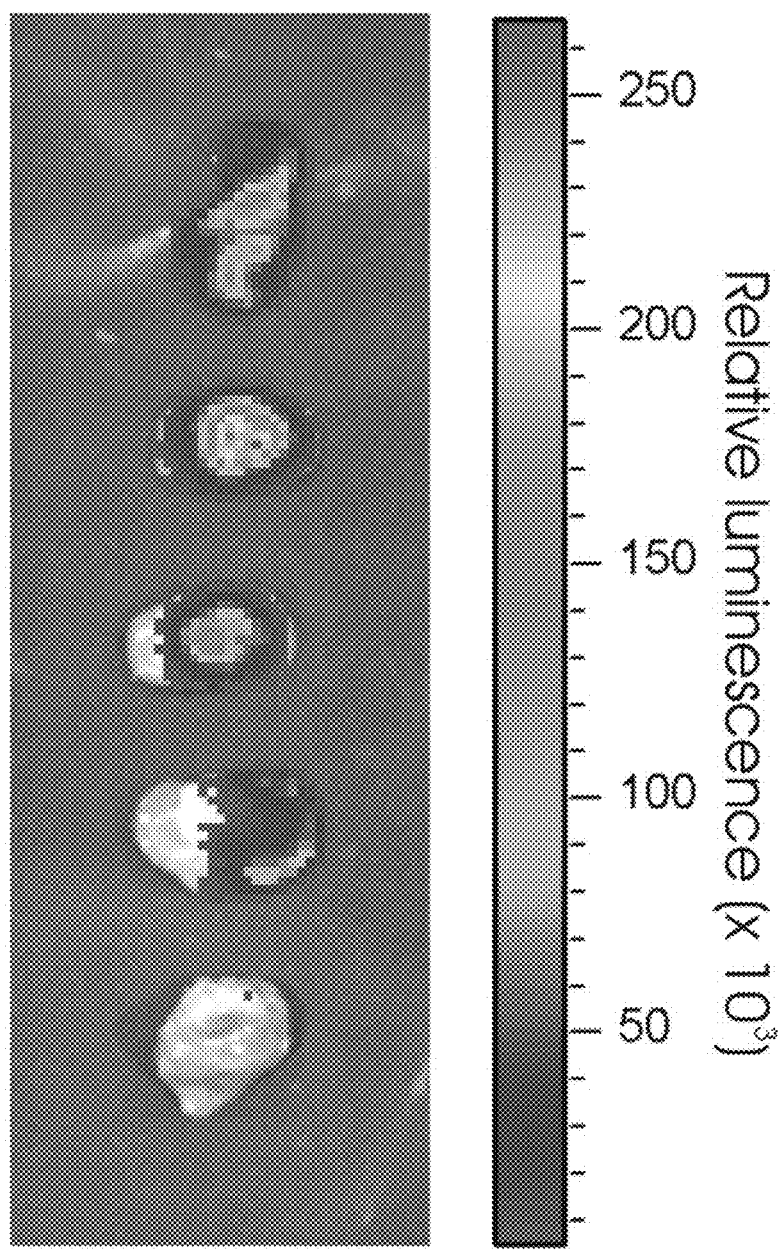
FIG. 16 is an image showing EGFR-targeted β-gal activity using a bioluminescence substrate.

Gli36Δ5 cells were implanted orthotopically in the brain of nude, athymic mice and allowed to propagate for 9 days. EGFR-targeted full length β-gal complex was prepared by mixing equal molar amounts of B-β-gal: B-EGF at room temperature for 1 hr. EGFR-targeted β-gal complex was intravenously injected into the tail vein of mice bearing orthotopic brain tumors and allowed to circulate for 4 hr. After 4 hr, the mice were euthanized and the brains excised and sectioned. Beta-glo (Promega) was topically applied to the brain and bioluminescence was captured after 3 min (FIG. 16). Brain sections were then embedded, cryosectioned, and counterstained with anti-EGFR to demonstrate cellular uptake and accumulation into Gli36Δ5 cells.

From the above description of the application, those skilled in the art will perceive improvements, changes and modifications. For example, it will be appreciated that the present application may find application in various other capacities, such as flow cytometry, affinity column chromatography, and the like. Such improvements, changes, and modifications are within the skill of those in the art and are intended to be covered by the appended claims. All patents, patent applications, and publication cited herein are incorporated by reference in their entirety.

Having described the invention, the following is claimed:

1. A composition for imaging a cell having a first biomarker and a second biomarker that is different than the first biomarker, the composition comprising:
   (a) a first imaging probe comprising: a first targeting moiety, an enzyme-activated contrast agent having an enzyme substrate, and a first linker region,
      wherein the first linker region links the enzyme-activated contrast agent to the first targeting moiety,
      wherein the enzyme-activated contrast agent is 1-(2-(β-Galactopyranosyloxy)propyl)-4,7,10-tris(carboxymethyl)-1,4,7,10-tetraazacyclododecane) gadolinium(III) (EGadMe), and
      wherein the first targeting moiety specifically complexes with the first biomarker; and
   (b) a second imaging probe comprising: a second targeting moiety, an activator molecule comprising β-galactosidase or fragments thereof, and a second linker region,
      wherein the second linker region links the activator molecule to the second targeting moiety,
      wherein the β-galactosidase or fragments thereof of the activator molecule activates the enzyme-activated contrast agent by enzymatic cleavage of the enzyme substrate of the enzyme-activated contrast agent,
      wherein the second targeting moiety is different than the first targeting moiety and specifically complexes with the second biomarker, and
   wherein the composition produces a detectable signal when the first targeting moiety of the first imaging probe and the second targeting moiety of the second imaging probe complex with first and second biomarkers of the cell to bring the first imaging probe and the second imaging probe in proximity to each other so that the enzyme substrate of the enzyme-activated contrast agent of the first imaging probe is cleaved by the β-galactosidase or fragments thereof of the second imaging probe to produce the detectable signal; and wherein the enzyme-activated contrast agent remains linked to the first targeting moiety via the first linker region after activation by the β-galactosidase or fragments thereof of the second imaging probe.

2. The composition of claim 1, wherein at least one of the first and second biomarkers is extracellular.

3. The composition of claim 1, wherein at least one of the first and second biomarkers is intracellular.

4. The composition of claim 1, wherein at least one of the first and second biomarkers is selected from the group consisting of a cellular protease, a kinase, a protein, a cell surface receptor, fatty acid, and lipid.

5. The composition of claim 1, wherein the first and second biomarkers are cancer cell surface receptors.

6. The composition of claim 1, the first and second targeting moiety being selected from the group consisting of polypeptides, polynucleotides, lipids, small molecules, elemental compounds, antibodies, and antibody fragments.

7. The composition of claim 1, wherein the linker region is a polymer.

8. The composition of claim 1, wherein at least one of the first and second linker regions comprising at least one peptide linker.

9. The composition of claim 8, the at least one peptide linker comprising a biotin-streptavidin-biotin linkage.

10. The composition of claim 1, the activator molecule including first and second enzyme fragments, the first and second enzyme fragments forming an activator complex that interacts with the enzyme-activated contrast agent to produce the detectable signal.

11. The composition of claim 1, wherein the enzyme-activated contrast agent comprises a self-immolative linker that connects a metal-ion chelator to the enzyme substrate, wherein the detectable signal is formed by enzymatic cleavage by the β-galactosidase or fragments thereof of the activator molecule of the second imaging probe.

12. A composition for imaging a cell having a first biomarker and a second biomarker that is different than the first biomarker, the composition comprising:

(a) a first imaging probe comprising: a first targeting moiety, an self-immolative enzyme-activated contrast agent having an enzyme substrate, and a first linker region, wherein the first linker region links the self-immolative enzyme-activated contrast agent to the first targeting moiety, wherein the self-immolative enzyme-activated contrast agent is 1-(2-(β-Galactopyranosyloxy)propyl)-4,7,10-tris(carboxymethyl)-1,4,7,10-tetraazacyclododecane) gadolinium(III) (EGadMe), and wherein the first targeting moiety specifically complexing with the first biomarker; and (b) a second imaging probe comprising: a second targeting moiety, an activator molecule comprising β-galactosidase or fragments thereof, and a second linker region, wherein the second linker region links the activator molecule to the second targeting moiety, wherein the β-galactosidase or fragments thereof of the activator molecule activates the self-immolative enzyme-activated contrast agent by enzymatic cleavage of the enzyme substrate of the self-immolative enzyme-activated contrast agent, and wherein the second targeting moiety is different than the first targeting moiety and specifically complexes with the second biomarker;

wherein the composition produces a detectable signal when the first targeting moiety of the first imaging probe and the second targeting moiety of the second imaging probe complex with first and second biomarkers of the cell to bring the first imaging probe and the second imaging probe in proximity to each other so that the enzyme substrate of the self-immolative enzyme activated contrast agent of the first imaging probe is cleaved by the β-galactosidase or fragments thereof of the second imaging probe to produce the detectable signal, wherein at least one of the first and second linker regions comprising a biotin-streptavidin-biotin linkage, and wherein the self-immolative enzyme-activated contrast agent remains linked to the first targeting moiety via the first linker region after activation by the enzyme or fragments thereof of the second imaging probe.

* * * * *